(12) United States Patent
Enrooth et al.

(10) Patent No.: US 9,126,052 B2
(45) Date of Patent: ***Sep. 8, 2015

(54) RATE INITIALIZATION AND OVERDRIVE PACING FOR CAPTURE THRESHOLD TESTING

(71) Applicant: Cardiac Pacemakers, Inc., St. Paul, MN (US)

(72) Inventors: Eric K. Enrooth, Lino Lakes, MN (US); Sunipa Saha, Shoreview, MN (US); Clayton S. Foster, Andover, MN (US); Yanting Dong, Lexington, KY (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/223,347

(22) Filed: Mar. 24, 2014

(65) Prior Publication Data

US 2014/0194943 A1  Jul. 10, 2014

Related U.S. Application Data

(63) Continuation of application No. 13/306,615, filed on Nov. 29, 2011, now Pat. No. 8,725,261.

(60) Provisional application No. 61/426,751, filed on Dec. 23, 2010.

(51) Int. Cl.
*A61N 1/37* (2006.01)

(52) U.S. Cl.
CPC ............... *A61N 1/371* (2013.01); *A61N 1/3714* (2013.01)

(58) Field of Classification Search
CPC ....................................................... A61N 1/371

USPC ........................................................... 607/28
See application file for complete search history.

(56) References Cited

U.S. PATENT DOCUMENTS

| | | | |
|---|---|---|---|
| 6,192,275 B1 | 2/2001 | Zhu et al. | |
| 6,427,085 B1 | 7/2002 | Boon et al. | |
| 6,430,441 B1 * | 8/2002 | Levine | 607/28 |
| 6,473,649 B1 | 10/2002 | Gryzwa et al. | |
| 7,062,327 B2 | 6/2006 | Bradley et al. | |
| 8,725,261 B2 * | 5/2014 | Enrooth et al. | 607/28 |
| 2008/0119902 A1 * | 5/2008 | Bohn et al. | 607/14 |

FOREIGN PATENT DOCUMENTS

| | | |
|---|---|---|
| EP | 0334681 A1 | 9/1989 |
| EP | 1118351 A2 | 7/2001 |

* cited by examiner

*Primary Examiner* — Eric D. Bertram
(74) *Attorney, Agent, or Firm* — Schwegman Lundberg & Woessner, P.A.

(57) ABSTRACT

Approaches for rate initialization and overdrive pacing used during capture threshold testing are described. Cardiac cycles are detected and the cardiac events of a cardiac chamber that occur during the cardiac cycles are monitored. The number of intrinsic beats in the cardiac events is counted. Initialization for a capture threshold test involves maintaining a pre-test pacing rate for the capture threshold test if the number of intrinsic beats in the cardiac events is less than a threshold. The pacing rate is increased for the capture threshold test if the number of intrinsic beats in the cardiac events is greater than the threshold.

11 Claims, 22 Drawing Sheets

RATE INITIALIZATION AND OVERDRIVE PACING FOR CAPTURE THRESHOLD TESTING

RELATED PATENT DOCUMENTS

This application is a continuation of U.S. application Ser. No. 13/306,615, filed on Nov. 29, 2011, now U.S. Pat. No. 8,725,261, which claims the benefit of Provisional Patent Application Ser. No. 61/426,751, filed on Dec. 23, 2010, to which priority is claimed pursuant to 35 U.S.C. §119(e) and which is hereby incorporated herein by reference.

FIELD

The present disclosure relates to implantable cardiac devices and methods of operating cardiac devices.

SUMMARY

Some of the embodiments described in this disclosure relate to methods used for capture threshold testing. According to some methods, cardiac cycles are detected and cardiac events of a cardiac chamber that occur during the cardiac cycles are monitored. The number of intrinsic beats in the cardiac events is counted. The pacing rate for a capture threshold test is initialized. A pre-test pacing rate is maintained for the capture threshold test if the number of intrinsic beats in the cardiac events is less than a threshold. The pacing rate is increased for the capture threshold test if the number of intrinsic beats in the cardiac events is greater than the threshold. The capture threshold test is performed using the initialized pacing rate.

In some implementations, if the pre-test rate is greater than a maximum rate, the rate initialization process is terminated.

Monitoring the cardiac events may include monitoring the cardiac events that occur during the cardiac cycles until a predetermined number of cardiac events have occurred.

Some implementations further include counting a number of consecutive atrial events that are intrinsic beats or fusion beats to determine an intrinsic/fusion beat count.

According to some aspects, after initializing the atrial pacing rate, the pacing rate during the capture threshold test is set by maintaining a previous pacing rate if the intrinsic/fusion beat count is less than a predetermined value; and increasing the previous pacing rate if the intrinsic/fusion beat count is greater than the predetermined value. Detecting cardiac cycles may be performed by detecting certain end events that signify the end of a cardiac cycle.

In some cases, the cardiac events are atrial events, the intrinsic beats are atrial intrinsic, and the pacing rate is an atrial pacing rate.

In some cases, the cardiac events are ventricular events, the intrinsic beats are ventricular intrinsic beats, and the pacing rate is a ventricular pacing rate.

Some embodiments discussed in this disclosure involve cardiac pacing devices. The device includes sensing circuitry configured to detect cardiac signals that include indications of cardiac events. A control processor is configured to monitor the cardiac events that occur during cardiac cycles and to count a number intrinsic beats in the cardiac events. The control processor includes circuitry configured to initialize a pacing rate for a capture threshold test (CTT). The control processor is configured to maintain a pre-test pacing rate during the capture threshold test if the number of intrinsic beats in the cardiac events is less than a threshold and to increase the pre-test pacing rate during the capture threshold test if the number of intrinsic beats in the cardiac events is greater than the threshold. The cardiac device includes pacing circuitry configured to deliver pacing during the capture threshold test using the initialized pacing rate.

In some cases, the control processor is configured to determine if the pre-test rate is greater than a maximum rate and to end the initialization if the pre-test rate is greater than the maximum rate.

According to some implementations, the control processor is configured to monitor the cardiac events that occur during the cardiac cycles until a number of cardiac events have occurred.

The control processor may be configured to count a number of consecutive cardiac events that are intrinsic beats or fusion beats to determine an intrinsic/fusion beat count. The previous pacing rate may be maintained if the intrinsic/fusion beat count is less than a predetermined value and the previous pacing rate may be increased if the intrinsic/fusion beat count is greater than the predetermined value.

In some cases, the cardiac events are atrial events, the intrinsic beats are atrial intrinsic beats, and the pacing rate is an atrial pacing rate.

In some cases, the cardiac events are ventricular events, the intrinsic beats are ventricular intrinsic beats, and the pacing rate is a ventricular pacing rate.

Some embodiments include a control processor configured to control the performance of a capture threshold test (CTT), the control processor is configured to count, during the CTT, a number of consecutive cardiac events that are intrinsic beats or fusion beats to determine an intrinsic/fusion beat count, the control processor further configured to maintain a previous pacing rate during the CTT if the intrinsic/fusion beat count is less than a predetermined value and to increase the previous pacing rate during the CTT if the intrinsic/fusion beat count is greater than the predetermined value.

The control processor may be configured to terminate the test if the paced cardiac rate is greater than a predetermined rate. The control processor may terminate the capture threshold test if a predetermined number of rate increases have occurred.

The above summary is not intended to describe each embodiment or every implementation of the present invention. Advantages and attainments, together with a more complete understanding will become apparent and appreciated by referring to the following detailed description and claims in conjunction with the accompanying drawings.

DESCRIPTION OF VARIOUS EMBODIMENTS

Figure 1:
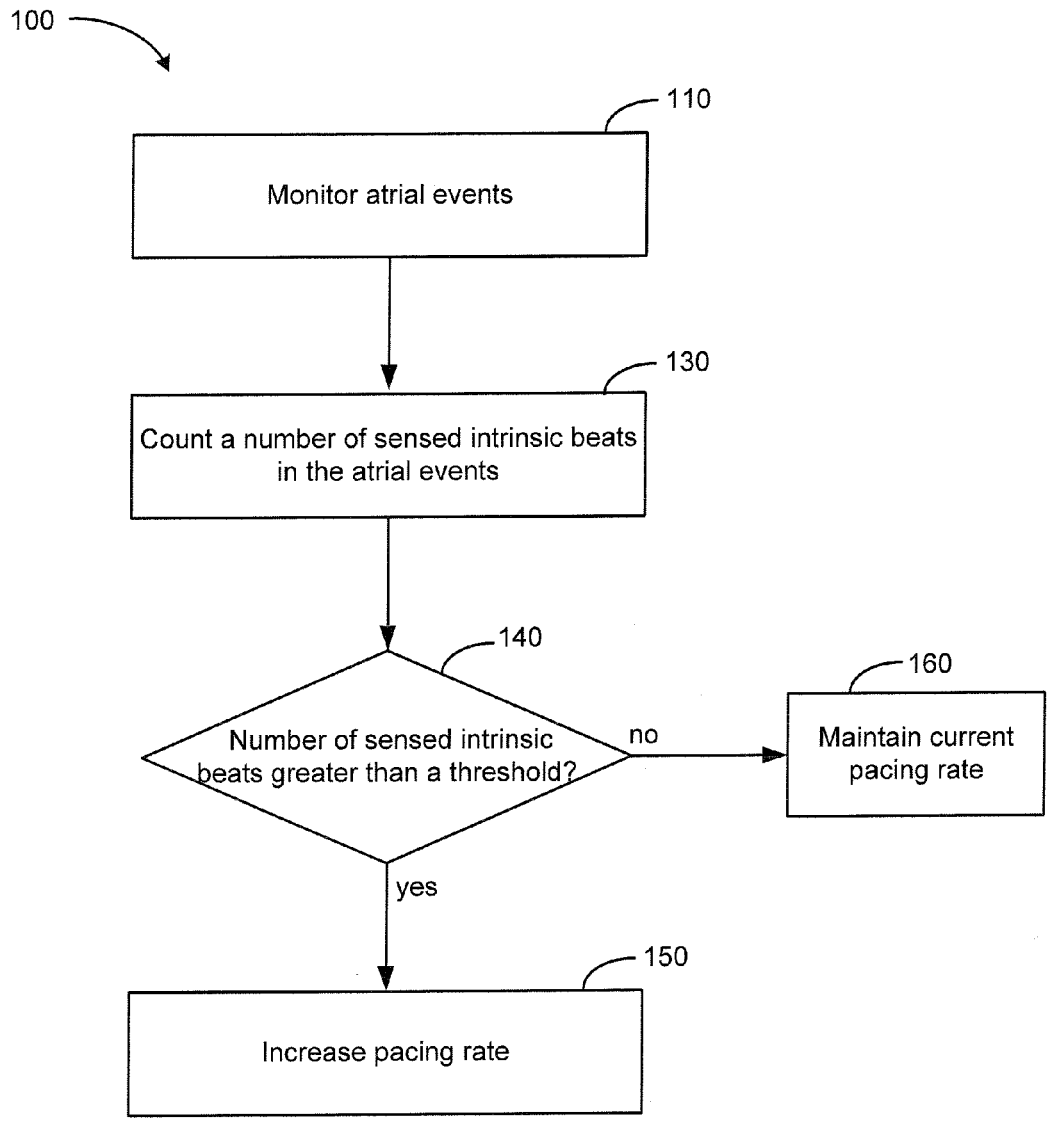
FIG. 1 is a flow diagram that illustrates a method of operating a cardiac device to initialize a pacing rate for atrial capture threshold testing in accordance with embodiments described herein.

Systems and devices described in this disclosure may include one of the structures described herein or any combination of structures described. Processes may include one of the functions described or combinations of functions. It is intended that such devices, systems, and/or processes need not include all of the structures and/or functions described, but may be implemented to include selected structures and/or functions. Such devices, systems and/or processes may be implemented to provide a variety of therapeutic or diagnostic features.

After delivery of a pacing pulse to a heart chamber, various cardiac responses to the pacing pulse are possible. In one scenario, the pacing pulse may generate a propagating wavefront of depolarization resulting in a contraction of the heart chamber. In this scenario, the pacing pulse is said to have captured the heart chamber. Capture of the heart chamber may occur if the pacing pulse has sufficient energy and is delivered during a non-refractory period. If the pacing pulse does not produce contraction of the chamber, the cardiac response is referred to as non-capture or loss of capture. Non-capture may occur, for example, if the pacing pulse energy is too low, and/or if the pacing pulse is delivered during a refractory period of the cardiac tissue. Fusion occurs when a depolarization initiated by a pace merges with an intrinsic depolarization.

Approaches for determining pacing response described herein rely on consistency in the morphology of the cardiac signal sensed following a pacing pulse to discriminate between noncapture, capture, and fusion responses. One or more features of the sensed cardiac signal following pacing, e.g., peak magnitude and/or peak timing, may be analyzed with respect to feature thresholds and/or timing intervals to determine the pacing response.

By way of example, the processes described herein may be used in a capture threshold test (CTT) used to determine the optimal energy for pacing. Capture detection allows the cardiac pacing device to adjust the energy level of pace pulses to correspond to the optimum energy expenditure that reliably produces a contraction. Embodiments described herein are directed to methods and systems for pacing response classification that distinguishes between capture, noncapture, and fusion. The pacing response classification processes described herein are based on the use of timing windows and amplitude thresholds to translate atrial response peak amplitude and timing information into capture, noncapture and fusion response classification.

The approaches for pacing response classification are described herein using atrial chamber response classification as an example. However, the approaches are equally applicable to any one or more cardiac chambers, e.g. left atrial chamber, right atrial chamber, left ventricular chamber, and/or right ventricular chamber. The examples based on atrial response detection discussed herein are extendable to other chambers as well.

Noncapture of the atrium by an atrial pace may allow retrograde conduction to occur when a depolarization wave initiated in a ventricle by a pacing pulse or intrinsic activation of the ventricle travels back to the atrium producing a retrograde P-wave. A pacing pulse delivered to the atrium will not result in capture if the atrial tissue is refractory due to a retrograde P-wave. Retrograde P-waves may inhibit accurate determination of the capture threshold during a capture threshold test. Further, retrograde conduction to the atrium may cause pacemaker mediated tachycardia (PMT).

Those skilled in the art will appreciate that reference to a CTT indicates a method of determining the capture threshold in one or more of the left atrium, right atrium, left ventricle, and right ventricle. In such a procedure, the pacemaker, automatically or upon command, initiates a search for the capture threshold of the selected heart chamber. The capture threshold is defined as the lowest pacing energy that consistently captures the heart. Other procedures for implementing a CTT may be utilized. In one example, the pacing energy may be increased in discrete steps until capture is detected. In another example, the pacing energy may be adjusted according to a binomial search pattern, or other search patterns.

In one example of an automatic CTT, the pacemaker delivers a sequence of pacing pulses to the heart and detects the cardiac pacing responses to the pace pulses. The energy of the pacing pulses may be decreased in discrete steps until a predetermined number of noncapture responses occur. The pacemaker may increase the stimulation energy in discrete steps until a predetermined number of capture responses occur to confirm the capture threshold. An atrial CTT may be performed using the pacing response classification, atrial sense and fusion management, retrograde management, and/or PMT management methods of embodiments described herein.

Capture threshold determination is distinguishable from automatic capture detection, a procedure that typically occurs during therapeutic pacing, rather than during test mode pacing. Automatic capture detection verifies that a delivered pace pulse results in a captured response. When a captured response is not detected following a pace pulse, the pacemaker may deliver a back up safety pace to ensure consistent pacing. If back up pacing is implemented, the back up pace may be delivered, for example, about 70-80 ms after the initial pace pulse. If a predetermined number of pace pulses delivered during normal pacing do not produce a captured response, the pacemaker may initiate a CTT to determine the capture threshold. Alternatively, if a predetermined number of pacing pulses do not produce a captured response, the pacemaker may adjust the pacing energy for the next pacing pulse.

FIG. 1 is a flow diagram that illustrates a method 100 of operating a cardiac device to initialize a pacing rate for an atrial CTT in accordance with embodiments described herein. The method 100 determines if the current pacing rate is at a rate high enough to avoid fusion during the atrial CTT. Prior to the commencement of the atrial CTT, the cardiac device monitors 110 atrial events that occur during a predetermined number of cardiac cycles. The atrial events may be paced atrial beats, intrinsic atrial beats, and/or fusion atrial beats, for example. In some cases, the device looks for a minimum number of the atrial events, e.g., about ten atrial events that occur during about fifteen cardiac cycles. If the minimum of atrial events is not detected during the cardiac cycles, then the atrial CTT may be terminated. Optionally, a failure code indicating the reason for the failure of the atrial CTT may be generated.

The number of the atrial events that are intrinsic atrial beats are counted 130. The device compares 140 the number of intrinsic atrial beats that occur during monitoring the atrial events to a threshold. In some implementations, the threshold is about six, so if the number of sensed intrinsic atrial beats is greater than or equal to about six intrinsic beats in about ten atrial events, there is sufficient intrinsic atrial activity to indicate that fusion is likely to occur during the atrial CTT. The cardiac device increases 150 the pacing rate to avoid fusion. For example, the device may increase the pacing rate by about ten beats per minute. If the number of sensed intrinsic atrial beats that occur during monitoring 110 the atrial events is less than the threshold, it is likely that the pacing rate is adequate to avoid fusion. The cardiac device maintains 160 the current pacing rate.

Figure 2A:
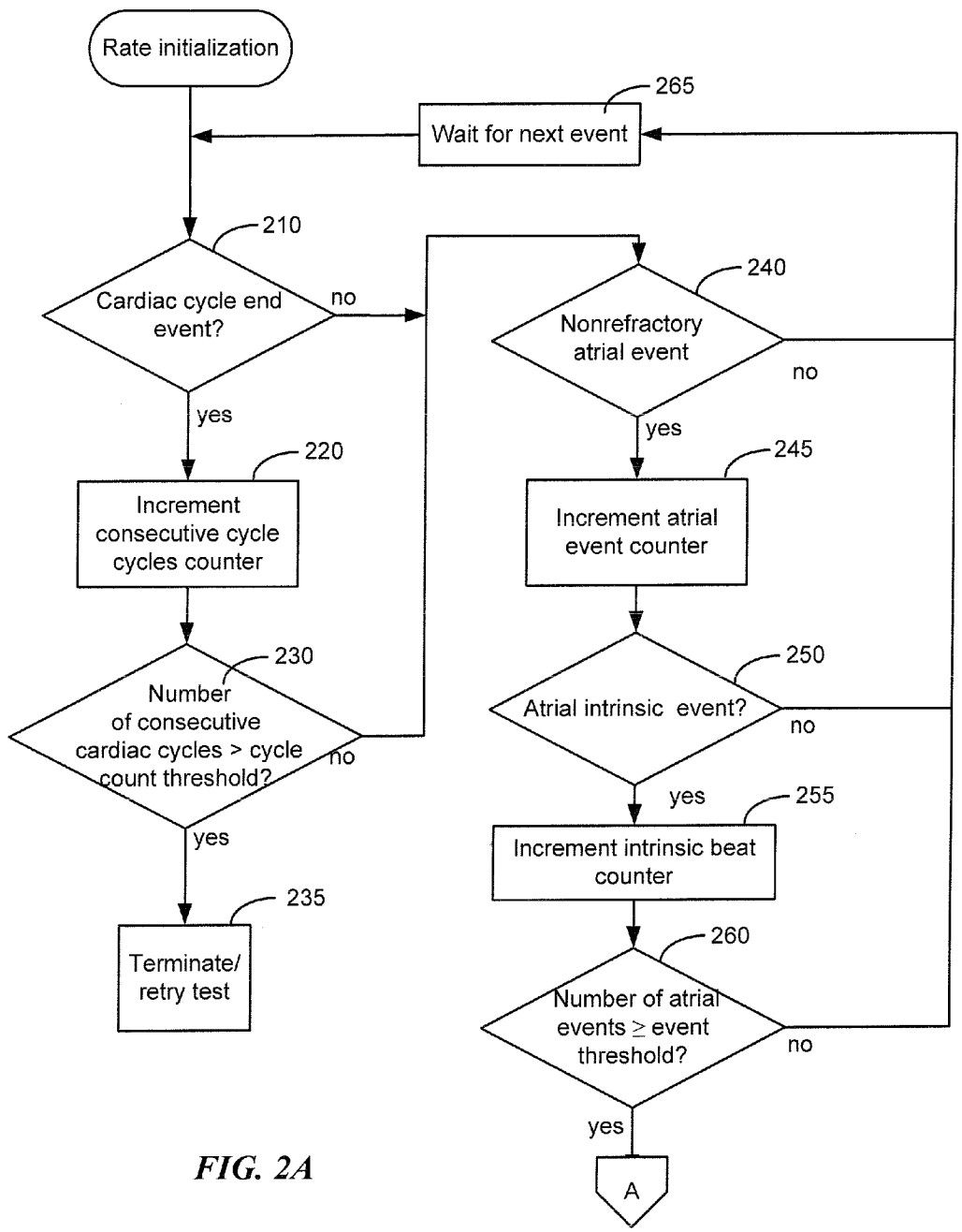
FIGS. 2A and 2B provide a flow diagram of a method of operating a cardiac device to initialize the atrial pacing rate prior to atrial capture threshold testing.
Figure 2B:
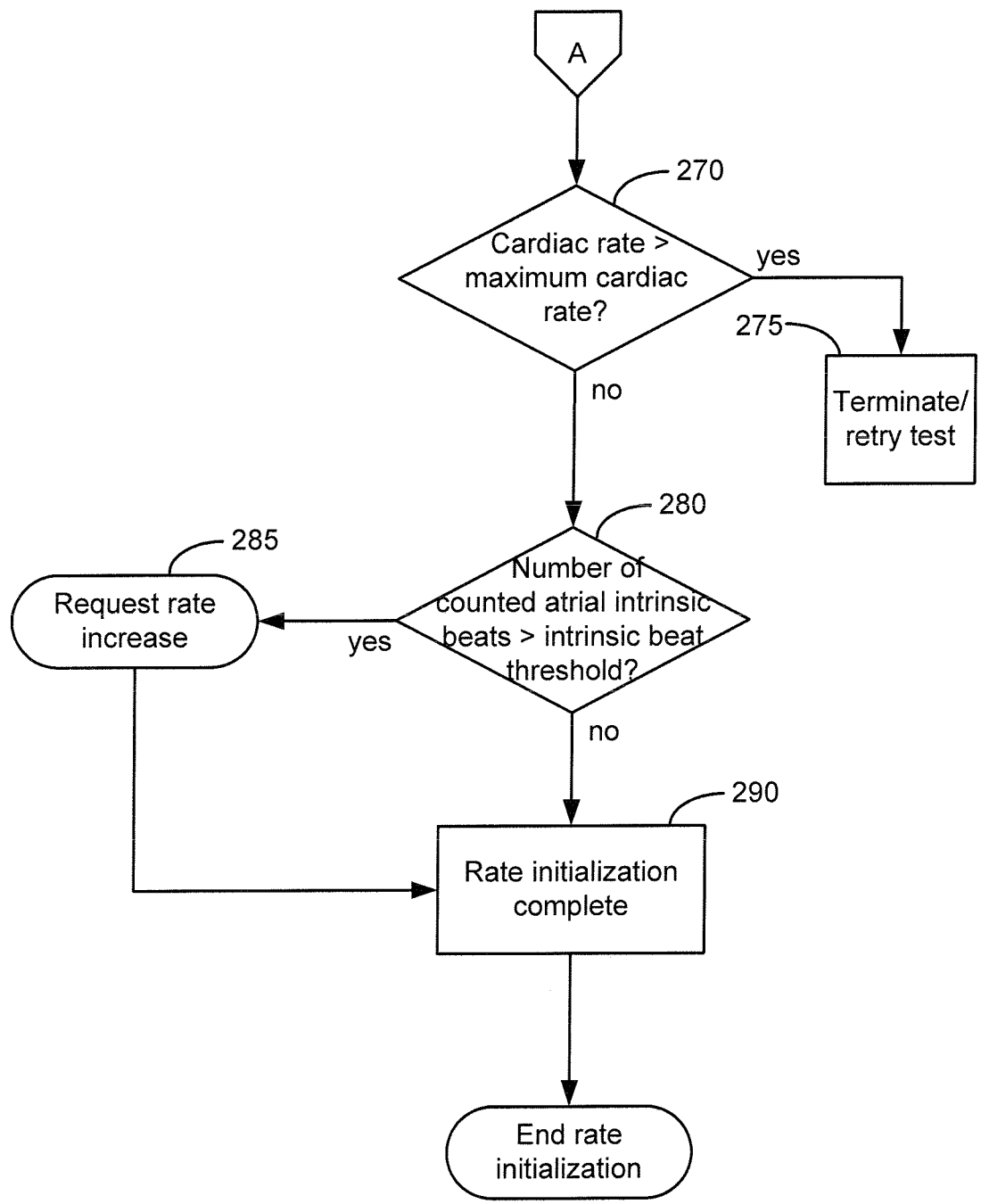

FIGS. 2A and 2B illustrate a more detailed flow diagram of a method of operating a cardiac device to initialize the atrial pacing rate prior to an atrial CTT. The device counts the number of consecutive cardiac cycles, counts the number of atrial events that occur during the consecutive cardiac cycles, and counts the number atrial events that are fusion or intrinsic events beats.

The device monitors cardiac cycles which are terminated by cardiac cycle end events. Cardiac cycle end events for various pacing modes are provided in Table 1.

TABLE 1

| Cardiac Cycle End Events | | |
|---|---|---|
| DDI(R) or DDD(R) (LV only) | DDI(R) or DDD(R) (Bi-V or | AAI(R) |
| RV sense | RV sense | A sense (non-refractory) |
| LV pace | RV pace | A pace |
| LV pace noise inhibited | RV pace noise inhibited | A pace noise inhibited |
| LV pace LVPP inhibited | | |

Where LV/RV/A pace noise inhibited is a pace that is scheduled, but inhibited due to the noise response of the device; LV pace LVPP inhibited is a pace that is inhibited if it would occur within a predetermined interval following a left ventricular depolarization. If a cardiac end event occurs 210, a consecutive cycle counter is incremented 220. The device compares 230 the number of consecutive cardiac cycles to a cycle count threshold. The cycle count threshold may be about 15 or 20, for example. If the number of consecutive cardiac cycles is greater than the cycle threshold without detecting enough atrial events, rate initialization for the atrial CTT may be terminated and/or retried 235. If, however, the number of consecutive cardiac cycles is less than the cycle count threshold, the method checks 240 to determine if the cardiac event was a non-refractory atrial event, i.e., an atrial fusion beat, non-refractory intrinsic atrial beat, or an atrial pace. Refractory atrial sensed beats are not included in the rate initialization process in this example.

If the cardiac event is not 240 an atrial event, the process waits 265 for the next event. If the cardiac event is 240 an atrial event, the atrial event counter is incremented 245. If the cardiac event is an atrial event and the atrial event is 250 an intrinsic atrial beat, the atrial intrinsic beat counter is incremented 255. If the atrial event is not an atrial intrinsic beat then the process waits 265 for the next event.

The device checks 260 to determine if the number of atrial events is greater than or equal to the atrial event threshold. The atrial event threshold may be about ten atrial events, for example. If the device determines 260 that the number of atrial events is less than the atrial event threshold, there are not enough atrial events to assess and the device waits 265 for another atrial event. The method continues to loop until the number of cardiac cycles exceeds the cycle threshold or the number of atrial events is greater than or equal 260 to the atrial event threshold. If the number of atrial events is equal to or greater than 260 the atrial event threshold, then a sufficient number of atrial events have occurred and the rate initialization process continues (see FIG. 2B).

The device determines the pre-test cardiac rate (or cardiac cycle interval) and checks to determine if the pacing rate can be increased for the CTT. If the pre-test cardiac rate is 270 above a maximum rate, e.g., about 110 beats per minute, then the atrial CTT is terminated and/or retried 275 at a later time. If, however, the pre-test cardiac rate is below or equal to 270 the maximum cardiac rate, the device proceeds with comparing 280 the number of counted atrial intrinsic beats (counted by the atrial intrinsic beat counter) to the atrial intrinsic beat threshold. In some cases, the atrial intrinsic beat threshold may be equal to about four or five, for example. If the number of atrial intrinsic beats is greater than the intrinsic beat threshold, the atrial pacing rate is too low to avoid atrial intrinsic and/or fusion beats during the atrial CTT. A rate increase is requested 285 and the rate initialization process is completed 290. If the number of atrial intrinsic beats is less than or equal to the intrinsic beat threshold, the atrial pacing rate is high enough to provide adequate pacing during the atrial CTT. The rate initialization process does not request 285 a rate increase and the current pacing rate is maintained. In some implementations, instead of keeping track of the number of intrinsic atrial beats in the atrial events, the device may instead keep track of the number of paces delivered and compare the number of paces delivered to a paced beat threshold.

Pacing rate initialization as discussed above is implemented to decrease the likelihood of fusion beats during an atrial CTT. Alternatively or additionally, the pacing rate may be adjusted during the atrial CTT if too many atrial sensed and/or atrial fusion beats occur during the CTT. An atrial intrinsic/fusion counter (I/F counter) keeps track of consecutive atrial beats that are either intrinsic beats or fusion beats.

The I/F counter is reset if an atrial pace occurs. If more than a predetermined number of atrial intrinsic or fusion beats (e.g., 5 atrial intrinsic or fusion beats of which at least 2 are atrial intrinsic beats) occur at any time after rate initialization, the device will perform a rate increase. Each rate increase increases the pacing rate by about 10 beats per minute (bpm) with a maximum number of rate increases in any CTT, e.g., about 2 rate increases, and a pacing rate upper limit, e.g., about 110 bpm. Rate increases may be applied to the filtered average rate rather than the lower rate limit (LRL), i.e., the rate is increased 10 beats per minute (bpm) above the current average rather than 10 bpm above the last pacing rate or the LRL.

Figure 3:
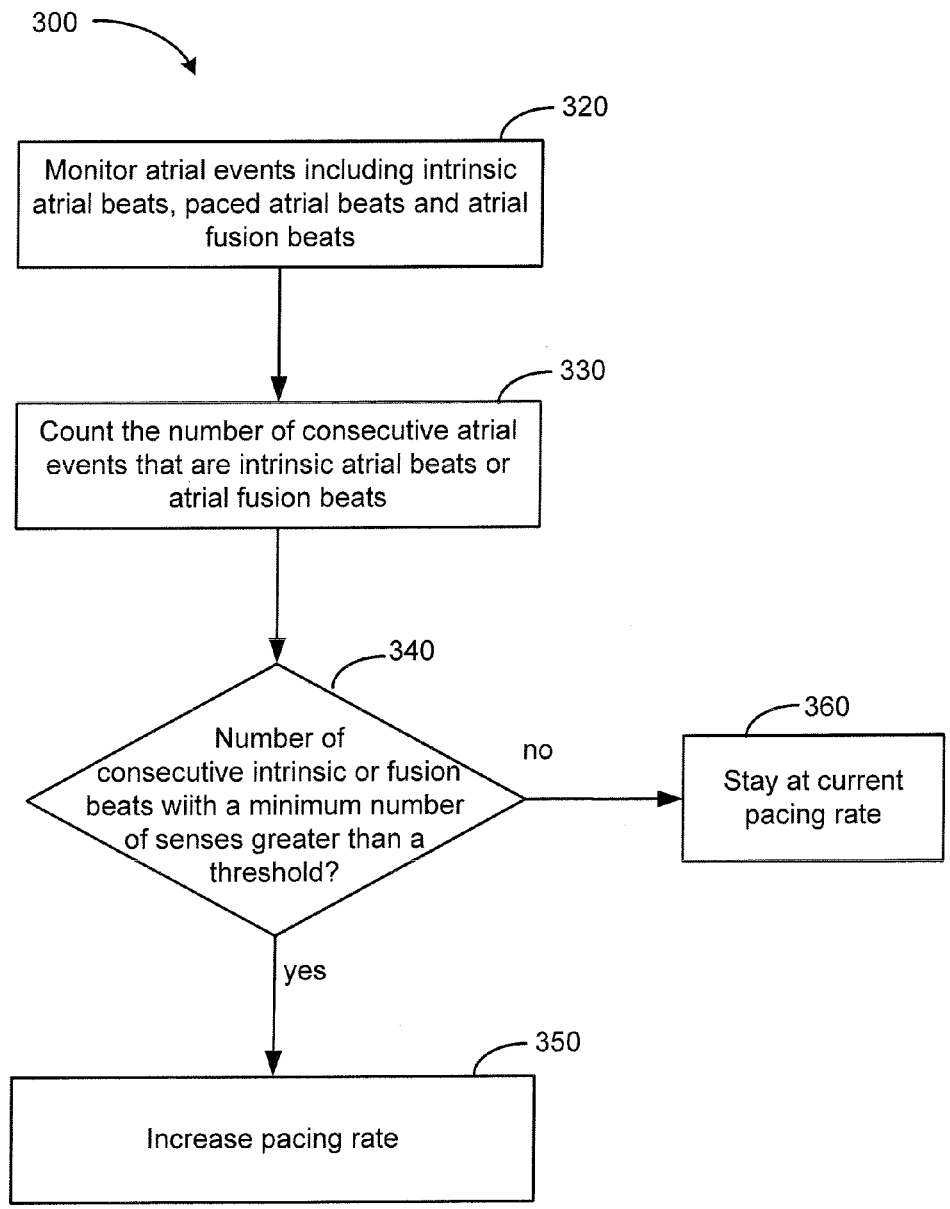
FIG. 3 is a flow diagram illustrating a method for atrial intrinsic/fusion beat management that may be implemented during an atrial capture threshold test.

FIG. 3 is a flow diagram illustrating a method 300 for atrial intrinsic/fusion beat management that may be implemented during an atrial CTT. During the CTT, atrial cardiac events are monitored 320. For example, the monitored atrial events can include intrinsic atrial beats, paced atrial beats, and atrial fusion beats. The device counts 330 the number of consecutive intrinsic atrial beats or atrial fusion beats. The intrinsic atrial beats are intrinsic beats that occur before an atrial pacing pulse is delivered for the cardiac cycle and these intrinsic beats may inhibit delivery of the scheduled pacing pulse. The device resets the counter when a paced atrial beat occurs. If the number of consecutive intrinsic atrial beats or atrial fusion beats is greater than an intrinsic/fusion threshold (I/F threshold), with a minimum number of intrinsic beats, the pacing rate is increased 350. If the number of consecutive intrinsic beats or fusion beats does not reach the I/F threshold, the current pacing rate is maintained 360.

FIG. 4 shows a more detailed flow diagram for intrinsic/fusion beat management which may be implemented during an atrial CTT to reduce the likelihood of occurrence of intrinsic or fusion beats during the CTT. After the occurrence of a cardiac event, the device determines 405 if the cardiac event is an event that ends a cardiac cycle. Cardiac cycle end events for various pacing modes are provided in Table I. If the cardiac event is a cardiac cycle end event, the device updates 407 the cardiac cycle time using the interval ended by the cardiac cycle end event. The cardiac cycle time is determined as a weighted average of cardiac cycle intervals. It will be appreciated that the cardiac rate is the inverse of the cardiac cycle time and that either parameter may be used as an indication of the rate of occurrence of cardiac events. In one implementation, the weighted average used to update the cardiac cycle time (CT) is calculated as Equation 1.

$$CT = A1 * \text{current value of } CT + A2 * \text{previous value of } CT \quad [1]$$

where A1 and A2 can be any appropriate coefficients, e.g. A1=0.25 and A2=0.75.

The CT may be smoothed using an infinite impulse response (IIR) filter implementing Equation 1 to lessen the effects of spurious fast beats.

The device determines 410 whether or not the present cardiac rate is greater than a maximum cardiac rate. The maximum cardiac rate may be about 110 bpm, for example. If the present cardiac rate, i.e., the CT determined using Equation 1, is not greater than a maximum rate, the device checks if the event is an atrial event 420 (FIG. 4B). If the present cardiac rate is greater than 410 a maximum cardiac rate, a consecutive high rate cycle counter (CHR counter) is incremented and a total high rate cycle counter (THR counter) is incremented. The CHR counter counts the number of consecutive beats that have a CT greater than the maximum rate. The THR counter counts the total number of beats (consecutive or non-consecutive) that have a CT greater than the maximum rate. If the CHR counter exceeds a maximum number (maxCHR) or if the THR counter exceeds a maximum number (maxTHR), then the threshold test terminates and may be attempted at a later time.

If neither CHR nor THR counters have reached their respective terminal counts, the device determines 420 (FIG. 4B) that the event is an atrial event. The device checks 422 if the atrial event is an atrial pace or a noise inhibited atrial pace. If the atrial event is not 422 an atrial pace or a noise inhibited atrial pace, the device determines 426 whether or not the atrial event is an atrial refractory sensed event, i.e., an atrial event sensed during a refractory period, such as the post ventricular atrial refractory period (PVARP). If the atrial event is 426 a refractory sensed event, the next scheduled atrial pace enforces a minimum interval 427 so that the next scheduled atrial pace occurs after the atrial tissue recovers and is no longer refractory following the refractory sensed event. For example, the next scheduled atrial pace may be delayed so that the next pace occurs at least about 300 ms after the sensed refractory atrial event.

If the atrial event is not 426, 428 a non-refractory intrinsic event, then the I/F counter is incremented 430. The I/F counter counts non-refractory intrinsic atrial beats and atrial fusion beats. If the atrial event is a non-refractory intrinsic event, then the atrial intrinsic event (AIE) counter is incremented. The I/F counter is checked 432 to determine if the I/F counter value is greater than an I/F threshold and the AIE counter is checked to determine if the AIE counter is greater than the AIE threshold. In some cases, the I/F threshold may be about 5 and the AIE threshold may be about 2. If the I/F count does not exceed 432 the I/F threshold or the AIE counter does not exceed the AIE threshold, then the process loops to look for the next cardiac event. If the number of intrinsic atrial beats and fusion beats counted by the I/F counter exceeds 432 the I/F threshold and the number of AIE beats exceeds the AIE threshold, then a rate increase is requested 434.

At step 422, if the atrial event is a delivered atrial pace or an atrial pace that was inhibited by noise, the device determines 424 whether or not the paced atrial rate is greater than a maximum atrial pacing rate. For example, the device determines if the atrial pacing rate corresponding to the interval between atrial paces (Ap-Ap) or the interval between an atrial pace and a noise inhibited atrial pace Ap-Ap (inhibited) is greater than the maximum pacing rate, e.g., about 110 bpm. If the atrial pacing rate exceeds the maximum atrial pacing rate, the CTT is terminated. If the atrial pacing rate is less than the maximum atrial pacing rate and fusion is not present, then the I/F and AIE counters are cleared 436 and the process loops to check the next cardiac event.

Figure 4A:
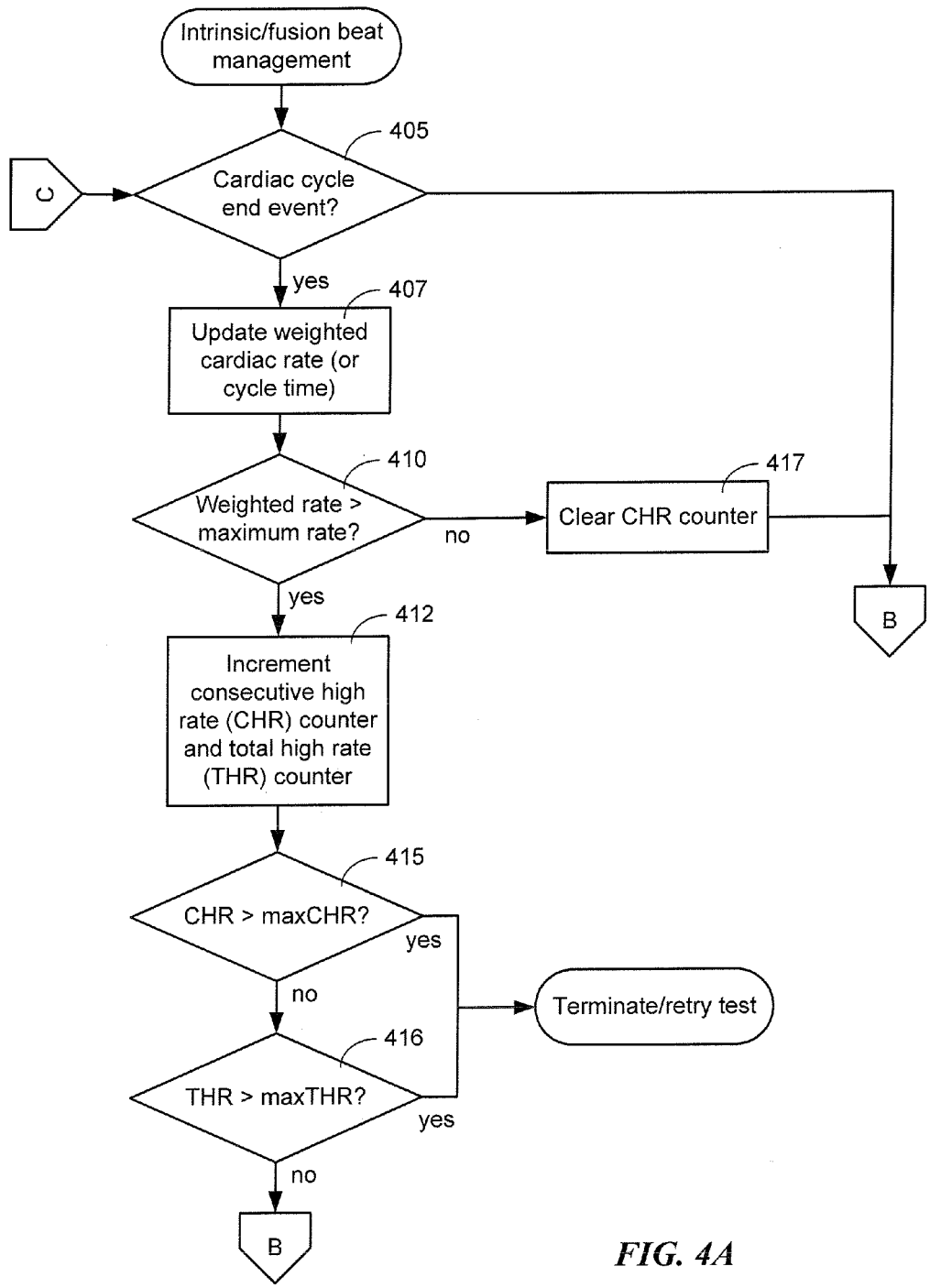
FIGS. 4A and 4B shows a more detailed flow diagram for intrinsic/fusion beat management which may be implemented during an atrial capture threshold test to reduce the likelihood of occurrence of intrinsic or fusion beats during the atrial capture threshold test.
Figure 4B:
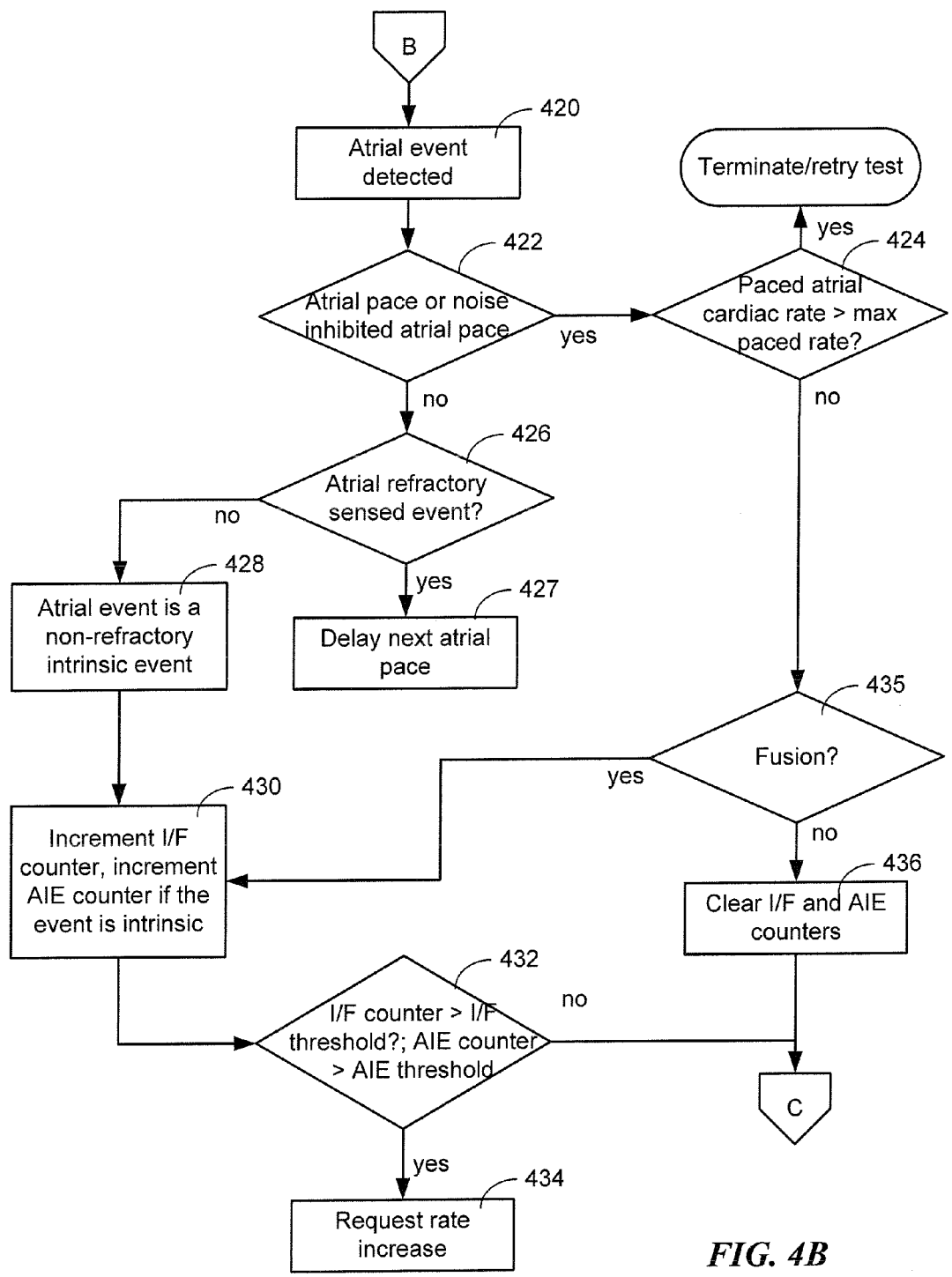
Figure 5:
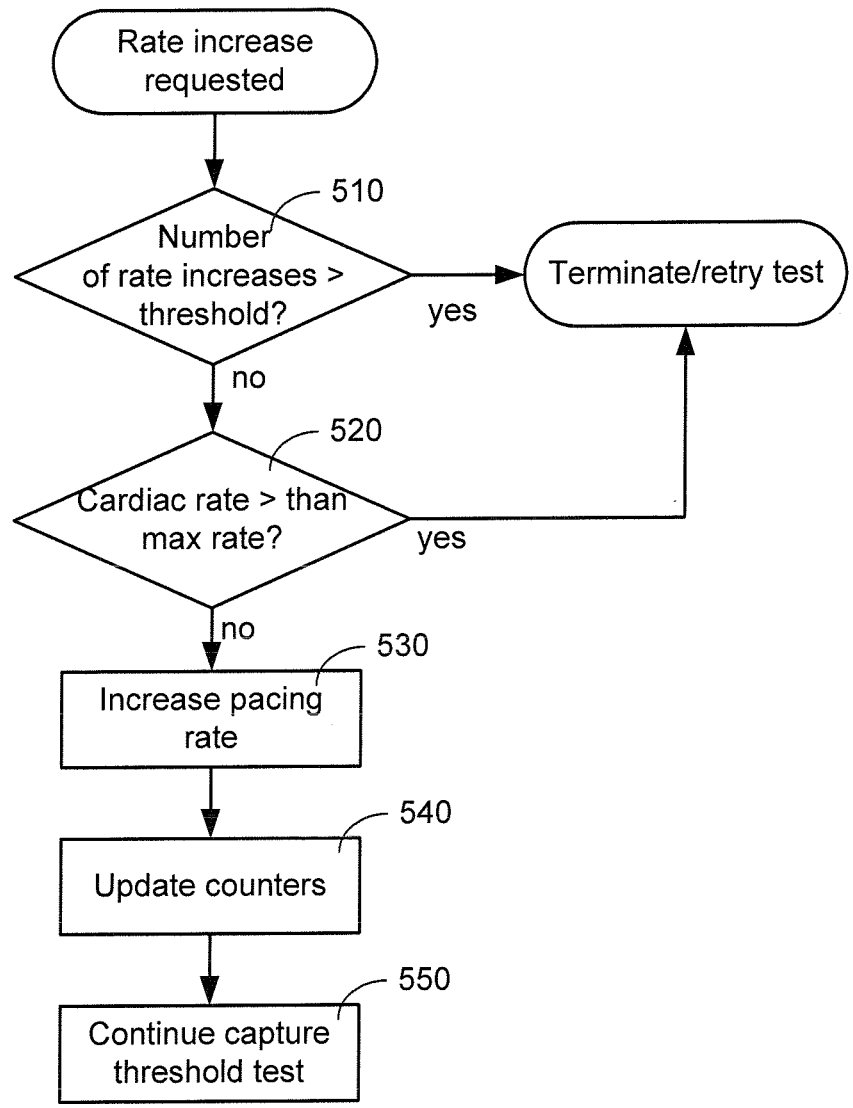
FIG. 5 illustrates a process for performing an atrial pacing rate increase after a rate increase has been requested during rate initialization prior to an atrial capture threshold test or during the atrial capture threshold test.

FIG. 5 illustrates a process for performing an atrial pacing rate increase after a rate increase has been requested during rate initialization prior to an atrial CTT (see, FIGS. 1, 2A and 2B) or during the atrial CTT (see, FIGS. 3, 4A and 4B). If a rate increase has been requested, the device determines 510 whether or not the number of rate increases in the current test is greater than a maximum rate increases threshold. For example, the maximum rate increases threshold may be equal to about two such that if there have already been two rate request increases, then no additional rate increases are performed and the CTT is terminated. If, however, the number of rate increases is below 510 the maximum rate increases threshold, the device determines 520 if the current rate, e.g., the cardiac rate determined using Equation 1 above, is greater than the maximum cardiac rate. The maximum cardiac rate may be about 110 bpm, for example. If the current rate is greater than 520 the maximum cardiac rate, the test is terminated and may be retried at a later time. If the current rate is less than 520 the maximum cardiac rate, the pacing rate is increased 530. For example, the atrial pacing rate may be increased by about 10 bpm above the weighted average value determined by Equation 1. The atrial pacing rate increase is capped by the maximum pacing rate. For example, if the maximum pacing rate is 110 bpm, the pacing rate increment is 10 bpm, and the current pacing rate is 105 bpm, then a pacing rate increase would only increase the pacing rate to 110 bpm. The I/F, AIE counters are cleared 540 and the number of rate increases counter is incremented. In addition, the capture counter, non-capture counter and I/F counter may also be cleared. The CTT proceeds 550 at the increased atrial rate. The timing windows and respiration modulation index (RMI) used for the CTT may be initialized or reinitialized after the rate increase.

Modulation of the cardiac response signal due to respiration causes the slight changes in the signal that may obstruct accurate cardiac response determination. The CTT may determine a respiration modulation index (RMI) used to adjust thresholds and/or templates, etc., for cardiac response determination, e.g., capture, non-capture, fusion thresholds. After initializing the RMI, e.g., at the beginning of each test, the RMI is used throughout that test. RMI is a measure of respiration affect on atrial evoked response (AER) amplitude. During RMI determination, the device gathers AER peak amplitude data for a number of atrial paces and/or for a maximum number of cardiac cycles. In some cases the device gathers AER peak amplitude data for about 12 atrial paces and or about 25 cardiac cycles. RMI may be calculated by using Equation [2].

$$RMI = [(\text{Avg AER amplitude of } X \text{ beats}) - (\text{Min AER amplitude of } X \text{ beats})]/(\text{Avg AER amplitude of } X \text{ beats}) \quad [2]$$

Successful RMI values may be between about 0 to 0.3, for example. Some values may still be determined to be successful if they do not fall within this specified range and an upper threshold may be invoked. For example, using the acceptable values 0 to 0.3, RMI values greater than 0.3 but less than 0.4 may be acceptable, but RMI may be set to 0.3 for capture detection threshold calculations. RMI values greater than or equal to 0.4 in this example, may signify either that fusion is present, giving wide variation in evoked response peak amplitudes, or that the algorithm is pacing sub-threshold. In some cases, even when the upper threshold limit is not met and/or when the RMI initialization does not complete in the maximum number of cardiac cycles, the device may continue with threshold tests if other criteria are met. For example, the criteria may include that one or more of the following occurrences: 1) there are less than a number e.g. 2, small evoked responses (0.35 mV, for example); 2) there is a recent successful threshold test; 3) the capture threshold is below a value such as 2.5 volts. Other criteria may also or alternatively be used. One or more of the criteria may be used to determine whether the device continues with threshold tests. The reasoning behind the use of the criteria is that RMI initialization may fail due to factors such as fusion or sub-threshold pacing. Fusion can be managed while sub-threshold pacing indicates a problem. Small evoked responses are often a sign of sub-threshold pacing, so too many sub threshold paces are undesirable. Because capture thresholds generally do not change suddenly, e.g., from 2.5 to 4 V within the "recent" test time of about 21 hours, it is assumed that if the previous threshold was <=2.5 V, the current RMI failure is caused by something other than sub-threshold pacing at 4.0 V. If these criteria are met, it may reasonably be concluded that fusion was the cause of the RMI failure and the test is allowed to continue with a default RMI value.

Figure 6:
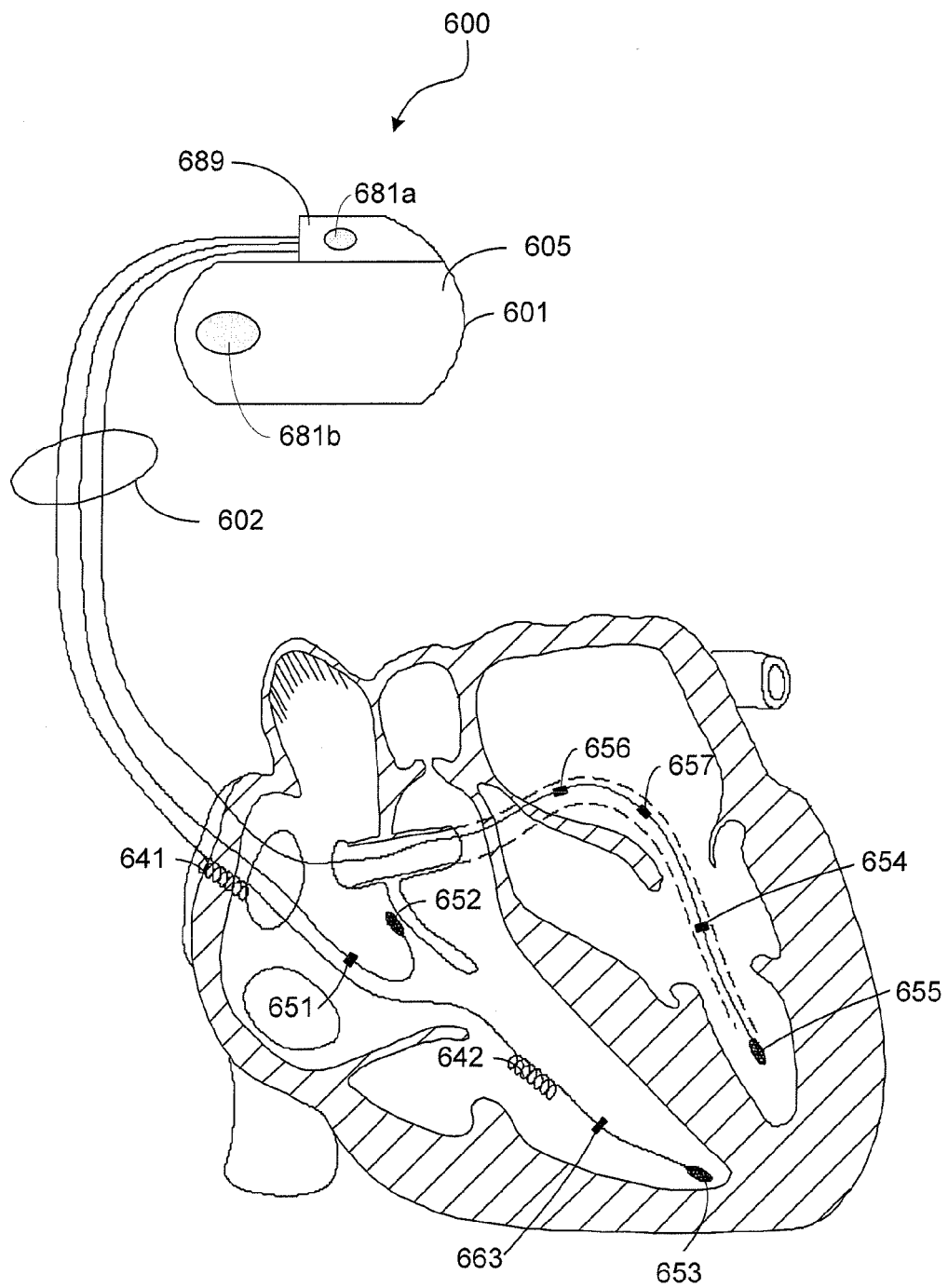
FIG. 6 illustrates an implantable cardiac rhythm management (CRM) system that may be used in connection with pacing methods in accordance with embodiments described herein.

Referring now to FIG. 6 of the drawings, there is shown a cardiac rhythm management system that may be used to implement atrial capture threshold testing according to embodiments described herein. The system in FIG. 6 includes an implantable cardiac device (ICD) 600 electrically and physically coupled to a lead system 602. The header and/or housing of the ICD 600 may incorporate one or more electrodes 681*a*, 681*b* used to provide electrical stimulation energy to the heart and to sense cardiac electrical activity.

The lead system 602 is used to detect electric cardiac signals produced by the heart and to provide electrical energy to the heart under certain predetermined conditions to treat cardiac arrhythmias. The lead system 602 may include one or more electrodes used for pacing, sensing, and/or cardioversion/defibrillation. In the embodiment shown in FIG. 6, the lead system 602 includes an intracardiac right ventricular (RV) lead system, an intracardiac right atrial (RA) lead system, an intracardiac left ventricular (LV)/left atrial (LA) lead system. The lead system 602 of FIG. 6 illustrates one embodiment that may be used in connection with the capture threshold testing methodologies described herein. Other arrangements may additionally or alternatively be used.

The lead system 602 may include intracardiac leads implanted in a human body with portions of the intracardiac leads inserted into a heart. The intracardiac leads include various electrodes positionable within the heart for sensing electrical activity of the heart and for delivering electrical stimulation energy to the heart, for example, pacing pulses and/or defibrillation shocks to treat various arrhythmias of the heart.

The lead system may include one or more extracardiac leads having electrodes, e.g., epicardial electrodes, positioned at locations outside the heart for sensing and pacing one or more heart chambers.

The right ventricular lead system illustrated in FIG. 6 includes an SVC-coil 641, an RV-coil 642, an RV-ring electrode 663, and an RV-tip electrode 653. The right ventricular lead system extends through the right atrium and into the right ventricle. In particular, the RV-tip electrode 653, RV-ring electrode 663, and RV-coil electrode 642 are positioned at appropriate locations within the right ventricle for sensing and delivering electrical stimulation pulses to the right ventricle. The SVC-coil 641 is positioned at an appropriate location within the right atrium chamber or a major vein leading to the right atrial chamber.

In one configuration, the RV-tip electrode 653 referenced to the can electrode 681*b* may be used to implement unipolar pacing and/or sensing in the right ventricle. Bipolar pacing and/or sensing in the right ventricle maybe implemented using the RV-tip and RV-ring electrodes 653, 663. In yet another configuration, the RV-ring 663 electrode may optionally be omitted, and bipolar pacing and/or sensing may be accomplished using the RV-tip electrode 653 and the RV-coil 642, for example. The right ventricular lead system may be configured as an integrated bipolar pace/shock lead. The RV-coil 642 and the SVC-coil 641 can be used as defibrillation electrodes.

Figure 16:
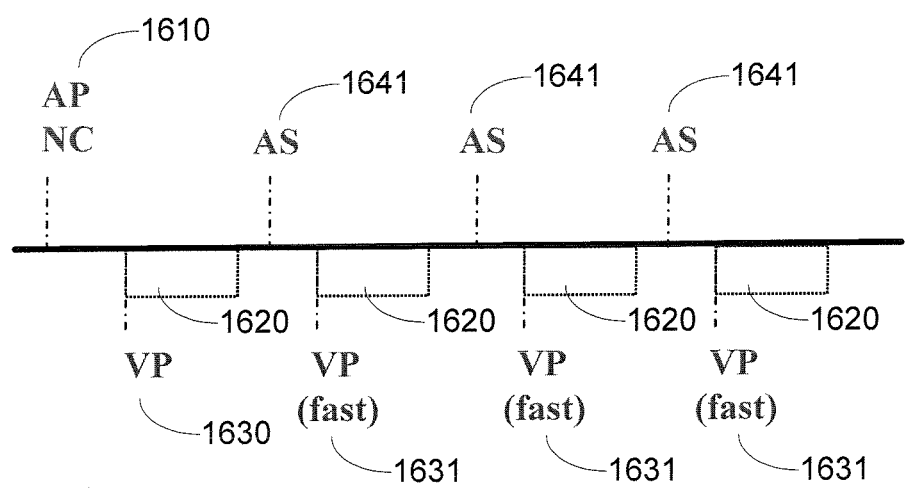
FIG. 16 is a timing diagram illustrating PMT caused by retrograde conduction.

The left heart lead includes an LV distal electrode 655 and an LV proximal electrode 654 located at appropriate locations in or about the left ventricle for sensing signals of the left ventricle and/or delivering electrical stimulation to left ventricle. In the example of FIG. 16, the left heart lead also includes optional left atrial electrodes 656, 657. The left heart lead may be guided into the right atrium via the superior vena cava. From the right atrium, the left heart lead may be deployed into the coronary sinus ostium and may be guided through the coronary sinus to a coronary vein. This vein is used as an access pathway for leads to reach the surfaces of the left atrium and/or left ventricle which are not directly accessible from the right side of the heart.

Unipolar pacing and/or sensing in the left ventricle may be implemented, for example, using the LV distal electrode 655 referenced to the can electrode 681b. The LV distal electrode 655 and the LV proximal electrode 654 may be used together as bipolar sense and/or pace electrodes for the left ventricle. The left heart lead and the right heart leads, in conjunction with the ICD 600, may be used to provide cardiac resynchronization therapy such that the ventricles and/or atria of the heart are paced substantially simultaneously, or in phased sequence, to provide enhanced cardiac pumping efficiency for patients suffering from congestive heart failure.

The right atrial lead includes a RA-tip electrode 652 and an RA-ring electrode 651 positioned at appropriate locations in the right atrium for sensing and pacing the right atrium. In one configuration, the RA-tip 652 referenced to the can electrode 681b, for example, may be used to provide unipolar pacing and/or sensing in the right atrium. In this configuration, RA-ring electrode 651 referenced to the can electrode 681b, for example, may be used to provide sensing of the RA evoked response. In another configuration, the RA-tip electrode 652 and the RA-ring electrode 651 may be used to effect bipolar pacing and/or sensing.

FIG. 6 illustrates one embodiment of left atrial electrodes 656, 657. Unipolar pacing and/or sensing of the left atrium may be accomplished, for example, using the LA distal electrode 657 to the can 681b pacing vector. The LA proximal 656 and LA distal 657 electrodes may be used together to implement bipolar pacing and/or sensing of the left atrium.

Figure 7:
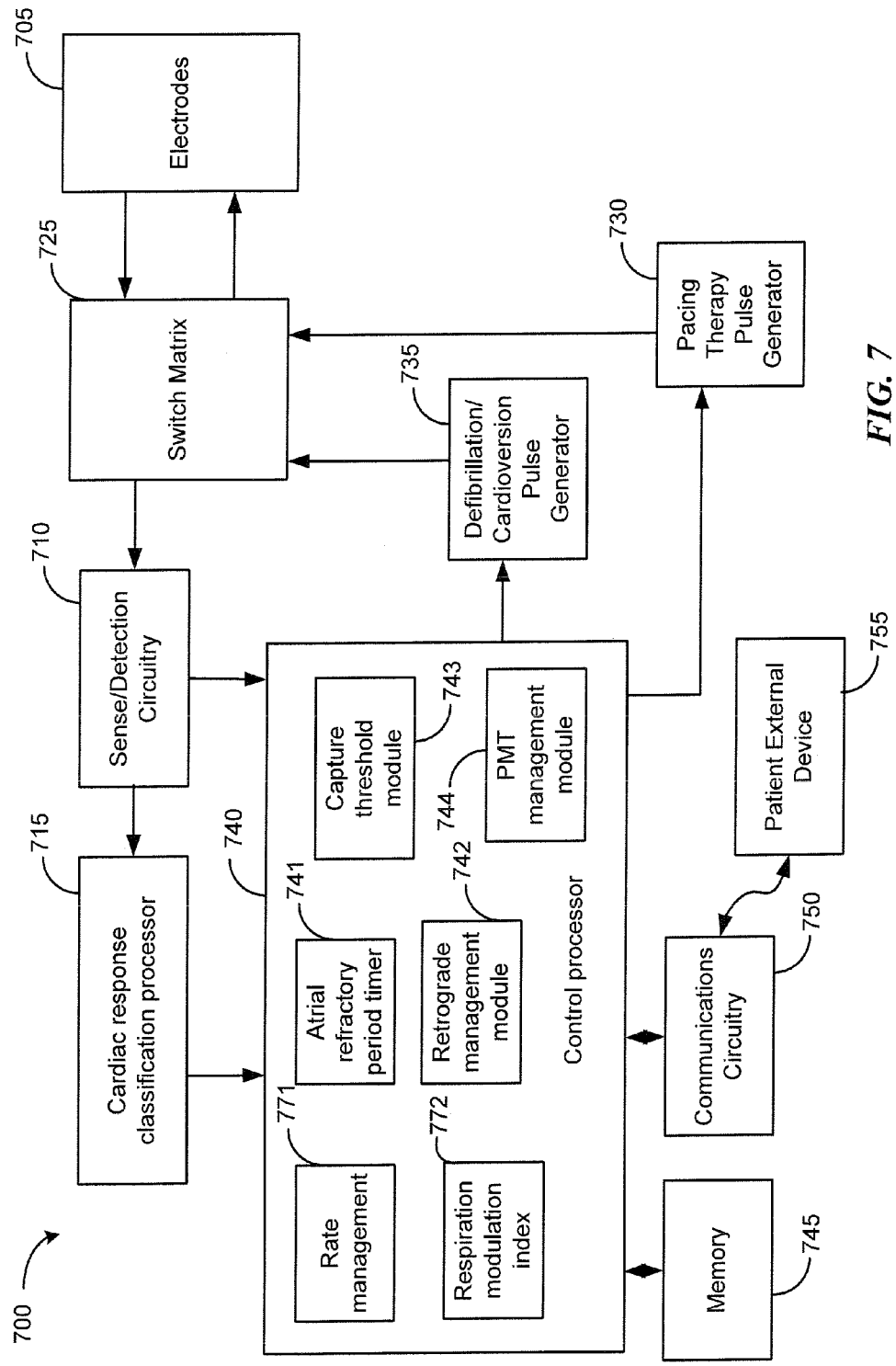
FIG. 7 is a block diagram of the circuitry of the implantable cardiac device according to embodiments described herein.

Referring now to FIG. 7, there is shown a block diagram of an embodiment of a cardiac system 700 suitable for implementing atrial capture threshold testing as described herein.

The cardiac system 700 includes a control processor 740 capable of controlling the delivery of pacing pulses or defibrillation shocks to the right ventricle, left ventricle, right atrium and/or left atrium. The pacing pulse generator 730 is configured to generate pacing pulses for treating bradyarrhythmia, for example, and/or for synchronizing the contractions of contralateral heart chambers using biatrial and/or biventricular pacing.

The control processor 740 may include an arrhythmia detector that operates to detect atrial or ventricular tachyarrhythmia or fibrillation. Under control of the control processor 740, the cardioversion/defibrillation pulse generator 735 is capable of generating high energy shocks to terminate the detected tachyarrhythmia episodes.

The pacing pulses and/or defibrillation shocks are delivered via multiple cardiac electrodes 705 electrically coupled to a heart and disposed at multiple locations within, on, or about the heart. One or more electrodes 705 may be disposed in, on, or about a heart chamber or at multiple sites of the heart chamber. The electrodes 705 are coupled to switch matrix 725 circuitry that is used to selectively couple the electrodes 705 to the sense circuitry 710 and the therapy pulse generators 730, 735.

The cardiac system 700 includes a pacing response classification (PRC) processor 715. In some embodiments, the PRC processor 715 is configured to discriminate between capture and non-capture. In some embodiments, the PRC processor is configured to discriminate between capture, non-capture and fusion. Pacing response classification is implemented by the PRC processor 715 for capture threshold testing and/or capture verification during therapeutic pacing. The PRC processor 715 is configured to determine various thresholds and intervals useful in the analysis of signals to determine the pacing response. For example, the PRC processor 715 may determine one or more of a pacing threshold interval (PTI), a pacing artifact threshold (PAT), and/or a capture detection threshold (CDT). Discrimination between capture, noncapture, and fusion is performed by the PRC processor 715 based on comparison of a cardiac signal sensed following a pacing pulse to one or more of the intervals or thresholds.

The control processor 740 includes a capture threshold module 743 that controls the operation of the cardiac system during capture threshold testing. The control processor 740 may include an atrial refractory period timer 741 for timing atrial refractory periods (ARP) and/or post ventricular atrial refractory periods (PVARP) following atrial and/or ventricular paces and/or senses. The control processor 740 may optionally include a retrograde management module 742 configured to control pacing during retrograde management pacing cycles. The control processor 740 may optionally include pacemaker mediated tachycardia (PMT) management module 744 configured to control pacing during PMT management pacing cycles. The control processor 740 may also contain a rate management module 771 and/or a respiration modulation index module 772.

The capture threshold module 743 controls the delivery of paces by the pacing therapy pulse generator 730 during therapeutic pacing and during capture threshold testing. To determine the capture threshold, the capture threshold module 743 may control the delivery of a sequence of pacing pulses that incrementally step down or step up the pacing energy until a capture threshold is determined. Prior to beginning the capture threshold test, the capture threshold module 743 may control pacing during an initialization procedure. During the initialization procedure, the PRC processor 715 operates to determine thresholds and intervals described herein that are useful in cardiac pacing response classification. The thresholds and intervals determined in the initiation procedure are then used to determine the pacing responses to the threshold test paces. Prior to beginning the capture threshold test, the rate management module 771 may perform processes to initialize the cardiac rate for the CTT. The RMI module 772 may determine the RMI used during the CTT.

The CRM system 700 is typically powered by an electrochemical battery (not shown). A memory 745 stores data and program commands used to implement the CTT approaches described herein along with other features. Data and program commands may be transferred between the CRM system 700 and a patient-external device 755 via telemetry-based communications circuitry 750.

FIG. 7 shows a CRM system 700 divided into functional blocks. It is understood by those skilled in the art that there exist many possible configurations in which these functional blocks can be arranged. The example depicted in FIG. 7 is one possible functional arrangement. Other arrangements are also possible. For example, more, fewer or different functional blocks may be used to describe a cardiac system suitable for implementing the processes described herein. In addition, although the CRM system 700 depicted in FIG. 7 contemplates the use of a programmable microprocessor-based logic circuit, other circuit implementations may be utilized.

Figure 8:
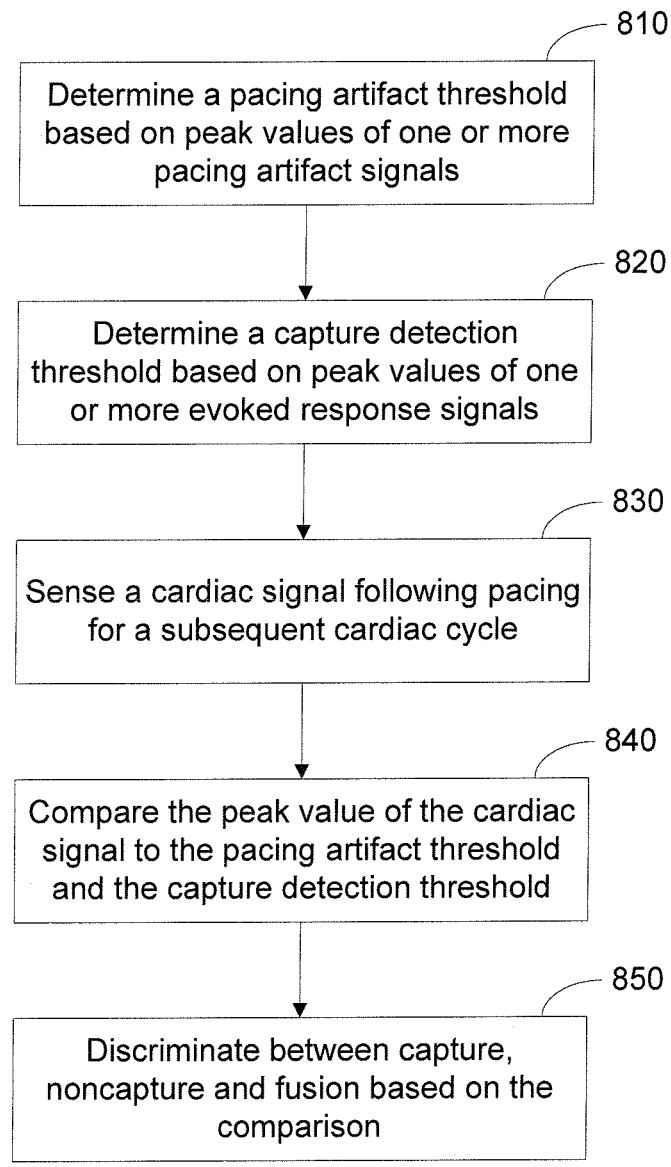
FIG. 8 is a flowchart illustrating a method for classifying the cardiac response to pacing that may be implemented by a CRM device in accordance with embodiments described herein.

FIG. 8 is a flowchart illustrating a method for classifying the cardiac response to pacing a heart chamber, such as an atrial heart chamber, that may be implemented by a CRM device in accordance with embodiments described herein. The time between a delivered atrial pace and the evoked response signal peak is substantially consistent. A peak timing interval (PTI) may be established for examining the cardiac signal to determine the pacing response. The magnitude of the peak may be used to classify the pacing response.

A method in accordance with one embodiment involves discriminating between capture, noncapture, and fusion based on comparison of a sensed cardiac signal peak to a capture detection threshold (CDT), a pacing artifact threshold (PAT), and a peak timing interval (PTI). The PAT is determined 810 based on peak values of atrial signals of one or more noncaptured cardiac cycles, e.g., about 2 to about 4 cardiac cycles. The signals used to determine the PAT may be sensed following sub-capture threshold paces following a capture threshold test, for example. The sensed atrial signals associated with noncapture are pacing artifact signals that have a morphology exhibiting a pacing artifact without the evoked response morphology produced by capture. In various implementations, the PAT may be based on a combination of the peak values of the signals associated with noncapture. For example, the PAT may be based on the peak magnitude of a most recent cardiac signal associated with capture, the largest one or more peak magnitudes of the signals associated with noncapture, a median value of the magnitudes of the signals associated with noncapture, a mean value of the magnitudes of the signals associated with noncapture, a weighted average of the magnitudes of the signals associated with noncapture, or other combination of the peak magnitudes of the signals associated with noncapture. The PAT may include an offset to take into account the variability of the peak magnitudes of the signals associated with noncapture. In one example, the PAT is set to a percentage, such as about 150%, of the peak magnitude of a most recent signal associated with noncapture.

A capture detection threshold (CDT) is determined 820 based on peak values of one or more evoked response signals, e.g., about 5 to about 10 signals, detected during one or more captured cardiac cycles. The signals used to determine the CDT follow supra capture threshold paces. The signals associated with capture exhibit a morphology that includes an evoked response signal having a superimposed pacing artifact signal. Similarly to the PAT determination described above, the CDT may be based on or a combination of the peak values of the signals associated with capture. The CDT may be based on a most recent peak magnitude of a signal associated with capture, the largest one or more peak magnitudes of the signals associated with capture, a median value of the peak magnitudes of the signals associated with capture, a mean value of the peak magnitudes of the signals associated with capture, or a weighted average of the peak magnitudes of the signals associated with capture, or other combination of the peak magnitudes of the signals associated with capture. The CDT may include an offset to take into account the variability of the peak magnitudes of the signals associated with capture. The use of a weighted average for the CDT provides such an offset, for example. In one embodiment, the CDT is set to a percentage of an average, e.g., about 70% of evoked response peak magnitudes.

A peak time interval (PTI) associated with an expected timing of the evoked response signal peak is used in conjunction with the PAT and the CDT. Discrimination between capture, noncapture, and fusion is based on comparison of the magnitude of the cardiac signal peak relative to the PAT and CDT and comparison of the timing of the cardiac signal peak relative to the PTI.

The PTI is determined based on the timing of peak values of one or more evoked response signals detected during one or more captured cardiac cycles. The signals used to determine the PTI follow supra capture threshold paces. The PTI may be determined based on the variability of the peak timing of the signals associated with capture, for example. A typical value of the PTI is about 9 ms, for example. The PTI may be based on a median value of the peak timings of the signals associated with capture, a mean value of the peak timings of the signals associated with capture, or a weighted average of the peak timings of the signals associated with capture, or other combination of the peak timings of the signals associated with capture. The PTI may include predetermined interval offsets on either side of a most recent, average, mean, or median timing value, for example, where the interval offsets take into account the variability of the peak timing of signals associated with capture.

A cardiac signal following a pacing pulse of a cardiac cycle subsequent to the noncaptured cardiac cycles and the captured cardiac cycles is sensed 830. A peak value of the sensed cardiac signal falling within the PTI is compared 840 to the PAT and to the CDT. The device discriminates 850 between capture, noncapture, and fusion based on the comparison. If the signal peak is less than the PAT, then the pacing response is determined to be noncapture. If the signal peak is greater than the CDT, then the pacing response is determined to be capture. If the signal peak falls between the PAT and the CDT, then the pacing response may be noncapture or may be fusion.

Figure 9A:
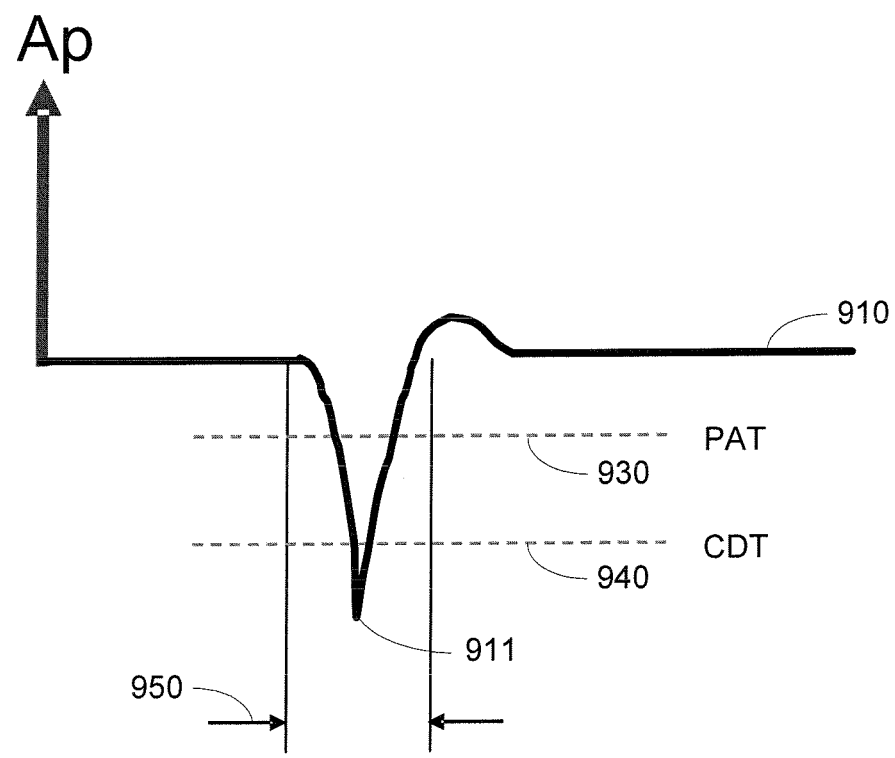
FIG. 9A is a graph illustrating the morphology of a cardiac signal sensed following an atrial pace.

FIG. 9A is a graph illustrating the morphology of a captured response signal 910 sensed following an atrial pace (Ap). The peak 911 of the cardiac signal 910 depicted in FIG. 9A has a magnitude (i.e., absolute value) larger than the PAT 930 and the CDT 940.

Figure 9B:
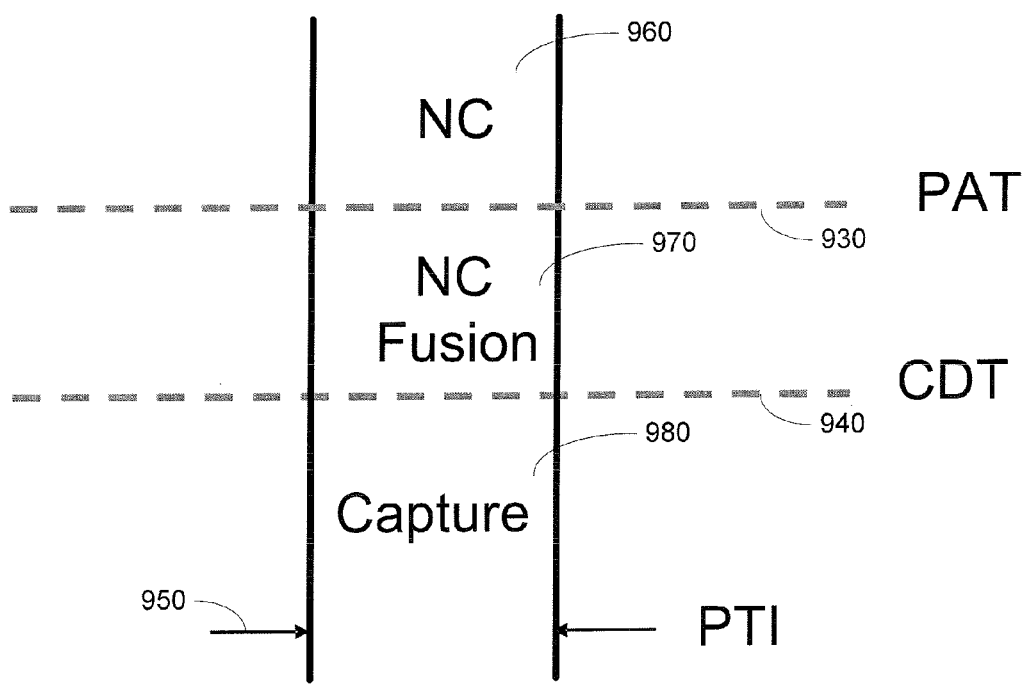
FIG. 9B is a diagram illustrating regions within the peak timing interval used in pacing response discrimination in accordance with embodiments described herein.

FIG. 9B is a diagram illustrating regions used in pacing response discrimination in accordance with one embodiment. FIG. 9B shows the PAT 930, the CDT 940, and the PTI 950 which define regions 960, 970, and 980 respectively associated with noncapture (NC), both noncapture and fusion, and capture. If the peak of a cardiac signal following pacing falls within a particular region 960, 970, 980, then the cardiac pacing response is classified as likely to be the type of response or responses associated with the region 960, 970, 980.

In one implementation, a counter for a particular type of response is incremented each time a peak falls within a region associated with the particular type of response. The counter increments may be integer or fractional increments. The counter increments may be based on the likelihood that a particular type of pacing response has occurred. For example, region 970 is associated with both noncapture and fusion. However, it may be more likely that a peak falling in region 970 is fusion rather than noncapture. If a peak falls within region 970, the fusion counter (I/F counter) may be incremented by 1 and the noncapture counter may be incremented by ½. In some scenarios, confirmation that a particular pacing response has been occurring may require several cardiac cycles. For example, confirmation of the particular type of pacing response may occur if a counter for the particular type of pacing response reaches a predetermined value.

Figure 10:
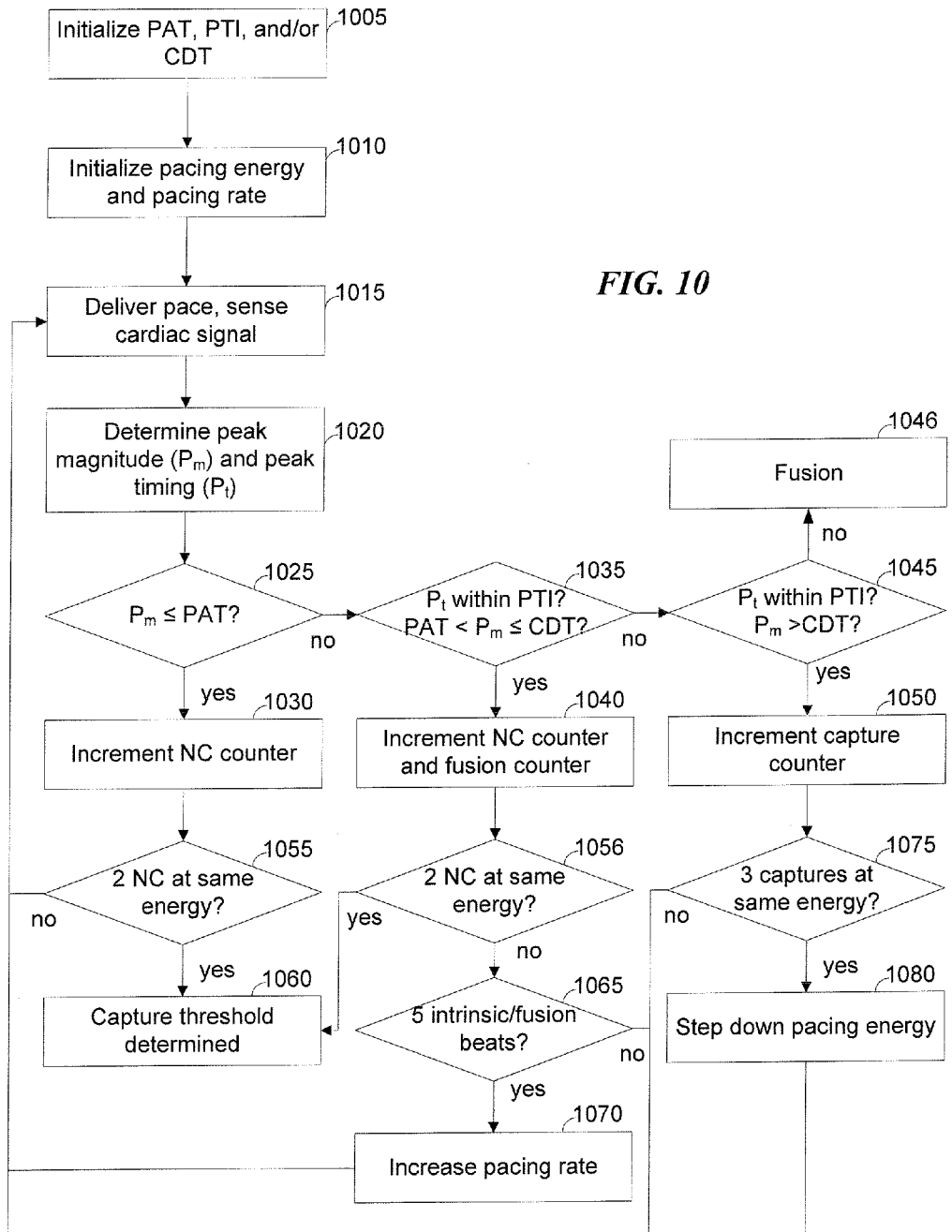
FIG. 10 is a flowchart illustrating step down capture threshold testing with pacing response classification based on the regions depicted in FIG. 9B in accordance with embodiments described herein.

FIG. 10 is a flowchart illustrating step down capture threshold testing with pacing response classification based on the regions depicted in FIG. 9B. The approaches described herein may advantageously be used in connection with capture threshold testing. Prior to beginning the step down test, the CDT and/or PTI are initialized 1005 based on the peak magnitudes of signals sensed following delivery of a series of supra capture threshold paces.

In one embodiment, the PAT is initialized to a predetermined value, such as about 0.3 mV prior to the capture threshold test. The CDT and PTI are initialized based on measured values of the peak magnitude and peak timing of captured signals. Initialization of the CDT and PTI prior to the test based on measured values provides patient specific values, enhancing the accuracy of capture testing. In addition, one or more of these parameters may be modified during and/or after the capture threshold test based on most recent peak timing and peak magnitude values to further enhance the test accuracy.

The pacing energy and the pacing rate are initialized 1010 for the test. A pace is delivered 1015 and the cardiac signal following the pace is sensed 1015. The peak magnitude ($P_M$) of the cardiac signal is determined 1020. If the peak magnitude is less than or equal to 1025 the PAT, then the pace did not capture the chamber and the noncapture counter is incremented 1030. If the peak timing is within the PTI and the peak magnitude is greater than the PAT but is less than or equal to the CDT 1035, then the pacing response may be noncapture or may be fusion. Both the noncapture counter and the fusion counter are incremented 1040. If the peak timing is within the PTI and the peak magnitude is greater than the CDT, then the pacing response is 1045 capture and the capture counter is incremented 1050. Otherwise, the response is determined 1046 to be fusion.

The amounts that the counters for each type of response are incremented may be integer or fractional amounts. In some implementations, the amount that a particular counter is incremented is associated with the likelihood that the type of pacing response occurred. For example, if the peak magnitude falls between the PAT and the CDT, fusion is more likely than noncapture. In this scenario, the fusion counter may be incremented by 1 and the noncapture counter incremented by ½.

If the noncapture counter reaches 1055, 1056 a predetermined value, e.g., about 2, for paces having the same energy, then loss of capture is confirmed and the capture threshold is determined 1060. If the fusion counter reaches 1065 a predetermined value, e.g., about 5 intrinsic beats or fusion beats, and at a least a minimum number of atrial intrinsic beats have occurred, e.g., about 2, then the pacing rate is increased 1070 to decrease the occurrence of intrinsic/fusion beats. If the capture counter reaches 1075 a predetermined value, e.g., about 3 for paces having the same energy, then the pacing energy is stepped down 1080 and the test continues until the capture threshold is determined 1060.

In some implementations, the PAT, CDT, and PTI may be initialized before the test and/or one or more of these parameters may be modified during the test, such as during every cardiac cycle, and/or may be modified after the test. The PAT may be reinitialized in the case of certain failures.

In one example, the peak timing and/or peak magnitude may be determined for the cardiac signal of each beat. The peak timing and/or peak magnitude may be combined with peak timings and magnitudes of one or more previous beats to dynamically modify the PTI and CDT during the test. Modifying the PTI and/or CDT during the test may be used to adapt to changing patient conditions, providing more accurate values for these parameters. The PAT may be modified after the test based on one or more noncaptured signals, detected after the capture threshold is determined. Modifying the PAT based on a particular patient's pacing artifact morphology allows for adaptation to changing patient conditions over time and provides more accurate pacing response classification.

Figure 11:
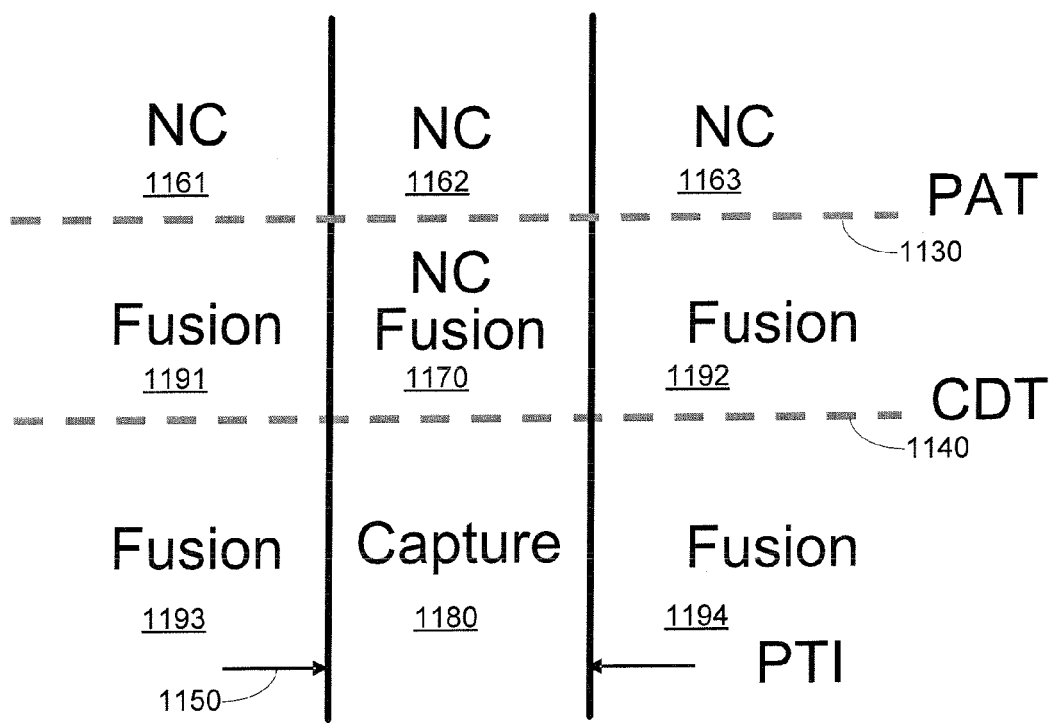
FIG. 11 is a diagram illustrating regions used in pacing response discrimination in accordance with embodiments described herein.

FIG. 11 is a diagram illustrating regions used in pacing response discrimination in accordance with another embodiment. Fusion beats usually exhibit large variations in peak timing of the cardiac signal when compared to captured beats. Regions corresponding to time intervals before and/or after the PTI may be used for fusion discrimination. FIG. 11 shows the PAT 1130, the CDT 1140, and the PTI 1150 which define regions 1161-1163 associated with noncapture, region 1170 associated with noncapture and fusion, region 1180 associated with capture, and regions 1191-1194 associated with fusion. If the peak of a cardiac signal following pacing falls within a particular region, then the cardiac pacing response is likely to be the type of response associated with the region.

As previously described, a counter for a particular type of response may be incremented each time a peak falls within a region associated with the particular type of response. The increments may be integer or fractional increments. The counter increments may be based on the likelihood that a particular type of pacing response has occurred. For example, region 1170 is associated with both noncapture and fusion. However, it may be more likely that a peak falling in region 1170 is fusion rather than noncapture. If a peak falls within region 1170, the fusion counter may be incremented by 1 and the noncapture may be incremented by ½. In some scenarios, confirmation that a particular pacing response has been occurring may require several cardiac cycles. For example, confirmation of the particular type of pacing response may occur if a counter for the particular type of pacing response reaches a predetermined value.

Figure 12A:
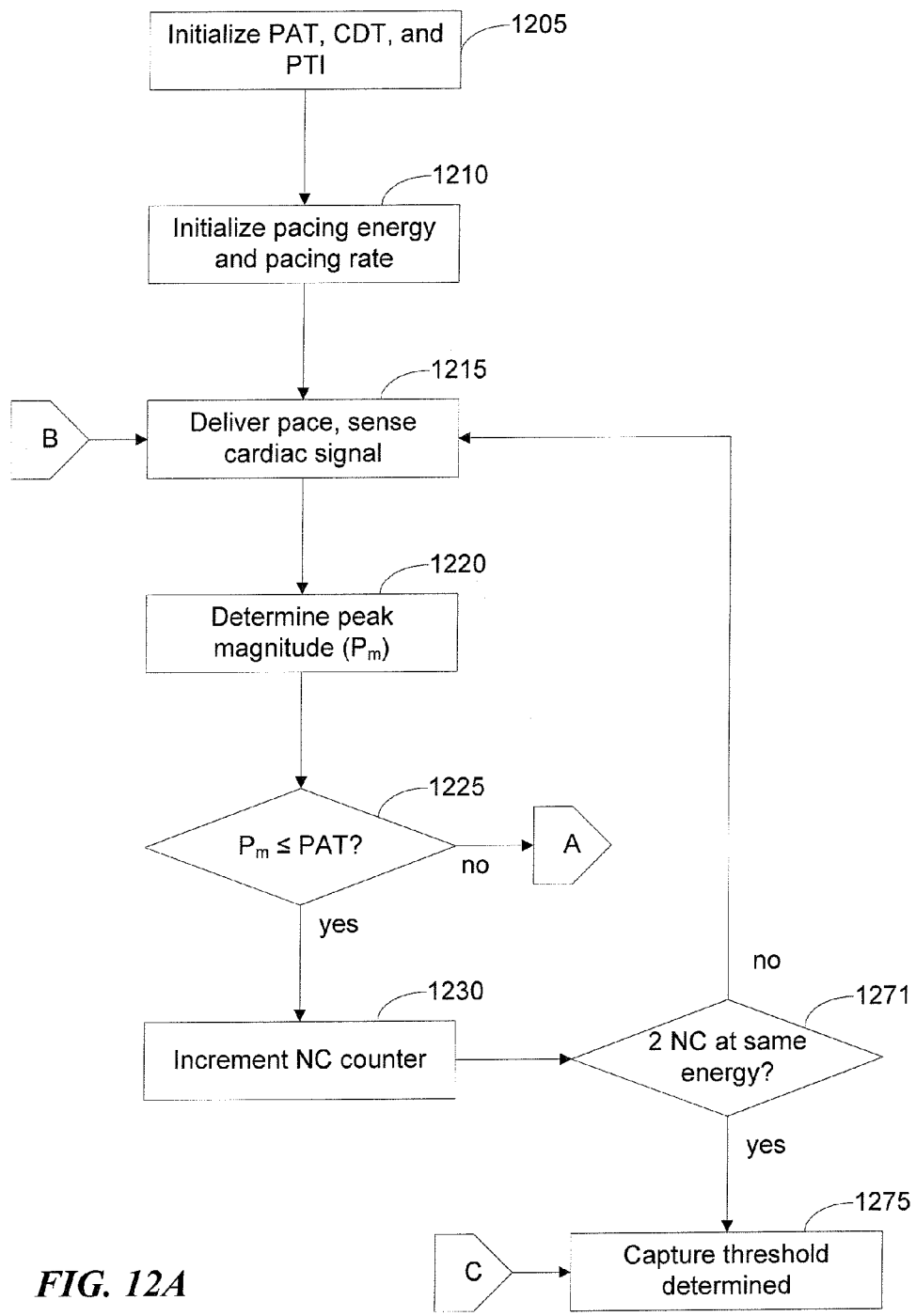
FIGS. 12A-12B illustrate a flowchart illustrating step down capture threshold testing with pacing response classification based on the regions depicted in FIG. 11 in accordance with embodiments described herein.
Figure 12B:
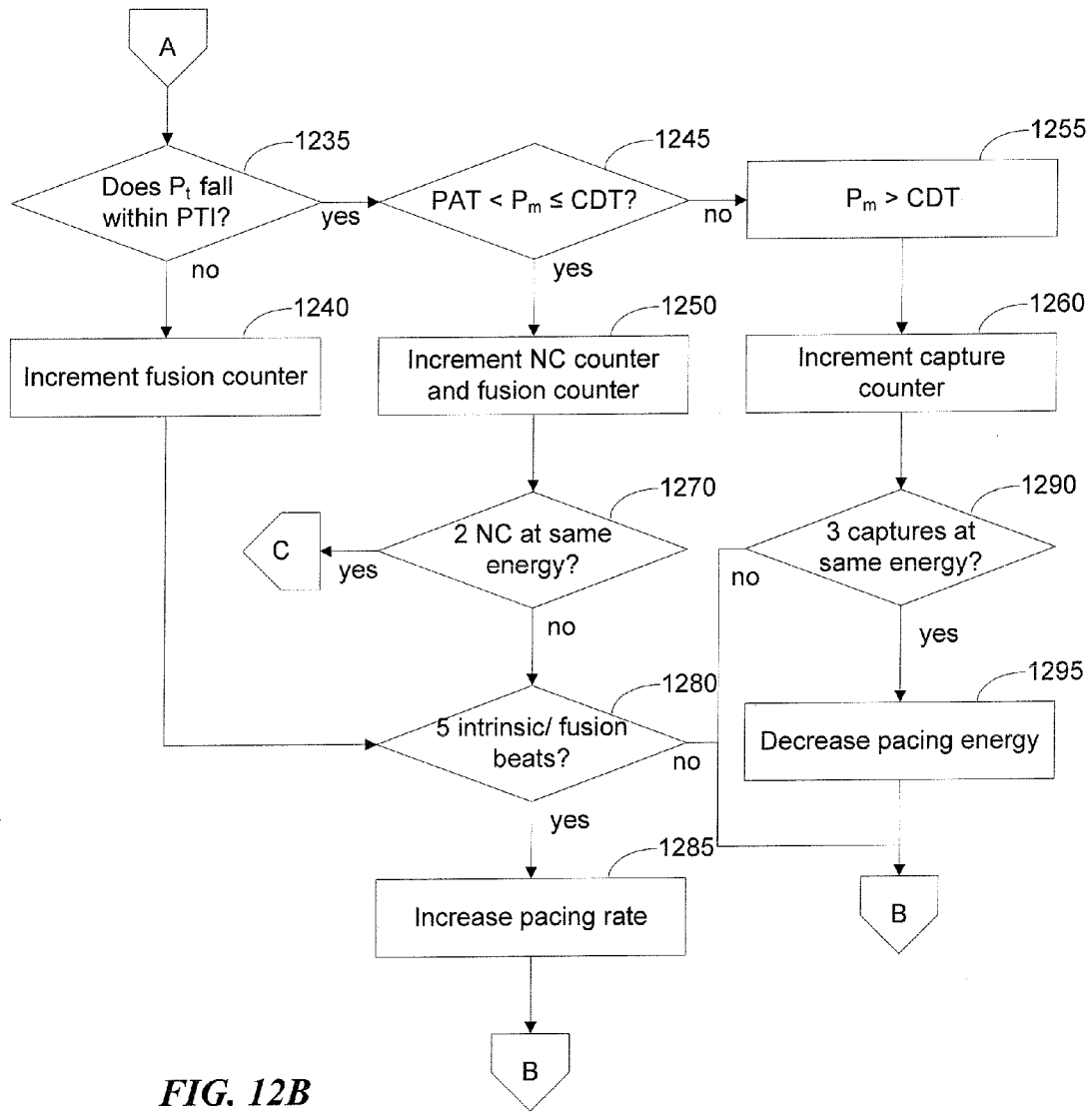

FIGS. 12A-12B illustrate a flowchart illustrating step down capture threshold testing with pacing response classification based on the regions depicted in FIG. 11. Prior to beginning the step down test, the PAT, CDT, and PTI are initialized 1205. The PAT is initialized to a predetermined value. The CDT is initialized based peak magnitudes, $P_m$, of signals sensed following delivery of supra capture threshold paces. PTI is initialized based on the peak timing, $P_t$, of signals sensed following delivery of supra capture threshold paces. The pacing energy and the pacing rate are initialized 1210 for the test.

A pace is delivered 1215 and the cardiac signal following the pace is sensed 1215. The peak magnitude, $P_m$, of the cardiac signal is determined 1220. If the peak magnitude is less than or equal to 1225 the PAT, then the pace did not capture the chamber and the noncapture counter is incremented 1230. If the peak magnitude is greater than the PAT and the timing of the peak does not fall 1235 within the PTI, then the pacing response is likely to be fusion and the fusion counter is incremented 1240.

If the timing of the peak falls within the PTI and the peak magnitude is greater than the PAT and less than or equal to 1245 the CDT, then the pacing response may be fusion or noncapture. The fusion counter and the noncapture counter are incremented 1250. If the peak magnitude is greater than the CDT, then the pacing response is 1255 capture and the capture counter is incremented 1260.

As previously described, the amounts that the counters for each type of response are incremented may be integer or fractional amounts. In some implementations, the amount that a particular counter is incremented is associated with the likelihood that the type of pacing response occurred. For example, if the peak magnitude falls between the PAT and the CDT, fusion is more likely than noncapture. In this scenario, the fusion counter may be incremented by 1 and the noncapture counter incremented by ½.

If the noncapture counter reaches 1270, 1271 a predetermined value, e.g., about 2, for paces having the same energy, then loss of capture is confirmed and the capture threshold is determined 1275. If the fusion counter reaches 1280 a predetermined value, e.g., about 5 intrinsic or fusion beats, with a minimum number of intrinsic beats, e.g., about 2, then the pacing rate is increased 1285 to avoid the occurrence of intrinsic/fusion beats. If the capture counter reaches 1290 a predetermined value, e.g., about 3 for paces having the same energy, then the pacing energy is stepped down 1295 and the test continues until the capture threshold is determined 1275. Following the capture threshold test, the PAT maybe updated based on the peak magnitude of one or more noncaptured signals.

During pacing, if noncapture occurs, retrograde conduction from an intrinsic or paced ventricular depolarization may cause a false noncapture detection on the next pacing cycle. Retrograde conduction during capture threshold testing, for example, may lead to erroneous capture threshold determination. Retrograde conduction may also cause undesirable fast pacing, denoted pacemaker mediated tachyarrhythmia (PMT). Some embodiments described herein include methods and systems that provide for management of retrograde conduction and PMT.

Figure 13:
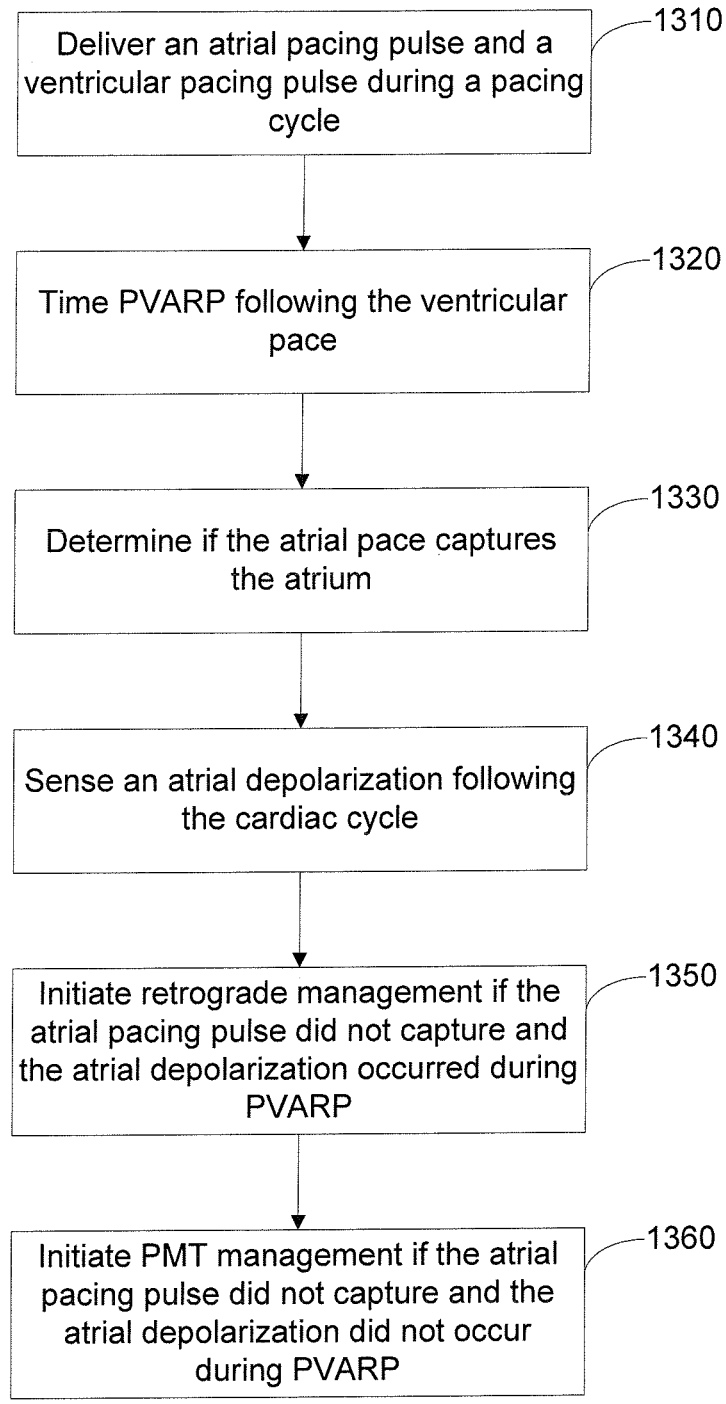
FIG. 13 is a flowchart that illustrates an approach implementable in a CRM system for retrograde conduction management and PMT management in accordance with embodiments described herein.

The flowchart of FIG. 13 illustrates an approach implementable in a CRM system for retrograde conduction management and PMT management in accordance with embodiments described herein. An atrial pace and a ventricular pace are delivered 1310 during a cardiac cycle. A post ventricular atrial refractory period (PVARP) is timed 1320 following the ventricular pace. The CRM system determines 1330 if the atrial pace captured the atrium. In some embodiments, capture may be detected based on comparison of peak magnitude and timing of the cardiac signal following pacing to the CDT, PAT, and PTI as described above. In other embodiments, capture may be determined using other capture detection methods known in the art.

If capture occurs, the depolarization associated with capture causes tissue refractoriness, making retrograde conduction unlikely. If noncapture occurs, the atrial tissue is not refractory after the pace and the ventricular depolarization may conduct retrogradely to the atrium. The system senses 1340 an atrial depolarization following the pacing cycle indicative of retrograde conduction. Retrograde management is initiated 1350 if the atrial pacing pulse did not capture and an atrial depolarization is sensed during the PVARP. PMT management is initiated 1360 if the atrial pacing pulse did not capture and an atrial depolarization is sensed after the PVARP.

Figure 14:
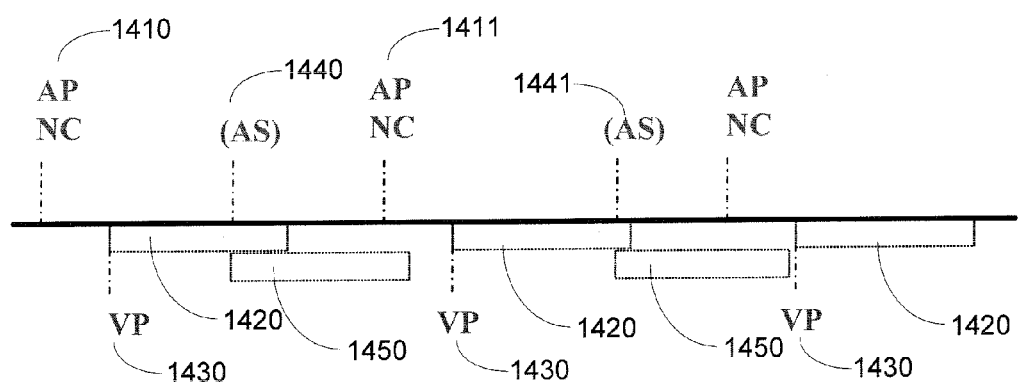
FIG. 14 is a timing diagram illustrating a scenario where loss of capture may be erroneously detected due to retrograde conduction.

The timing diagram of FIG. 14 illustrates a scenario where noncapture is erroneously detected due to retrograde conduction. A noncaptured atrial pace 1410 and a ventricular pace 1430 are delivered during a first cardiac cycle. A PVARP 1420 is timed is following the ventricular pace 1430. In this cycle, the atrial pace may be accurately detected as noncapture. However, confirmation of the loss of capture during a capture threshold test typically requires more than one noncaptured pace, such as several noncaptured paces detected consecutively or within a short period of time. If a noncapture event was caused by transient effects, such as noise, rather than by the decrease in the pacing energy, then loss of capture would not be confirmed because subsequent paces would be captured and the test would continue. However, a pattern of retrograde conduction may be initiated by the noncaptured pace, causing a single noncaptured pace to result in an erroneous loss of capture confirmation as described below.

Because the atrial pace 1410 did not produce capture, the depolarization caused by the ventricular pace causes retrograde conduction to the atrium. The retrograde conduction produces an atrial depolarization 1440 causing the atrial tissue to become refractory. The atrial depolarization 1440 does not initiate a new pacing cycle because it occurs during PVARP 1420. The atrial pace 1411 for the next cycle is delivered during the tissue refractory period 1450. Because the atrial pace 1411 is delivered while the tissue is refractory, the pace 1411 is detected as noncapture. During a capture threshold test, the noncaptured atrial pace causes a false detection of noncapture because the noncapture is the result of tissue refractoriness following retrograde conduction rather than the change in the pacing energy level. Noncapture of the atrial pace 1411 during the second cardiac cycle again causes retrograde conduction, an atrial depolarization 1441, and tissue refractoriness. The pattern of false noncapture detection and retrograde conduction may continue resulting in a confirmation of loss of capture and an erroneous capture threshold measurement.

Figure 15:
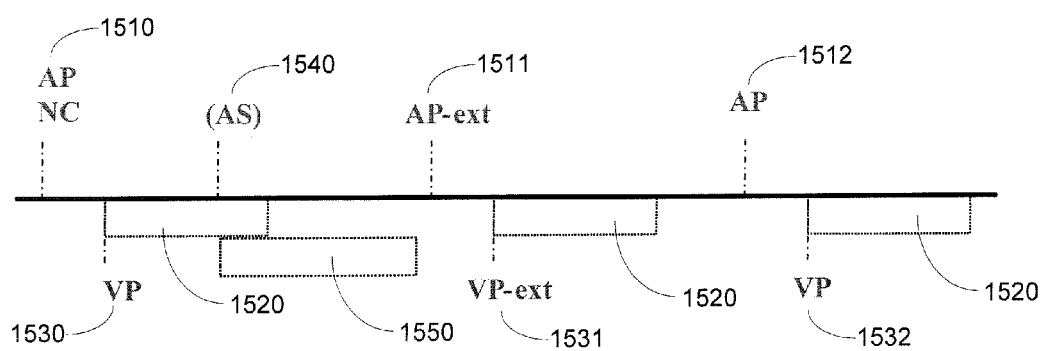
FIG. 15 is a timing diagram illustrating retrograde management in accordance with embodiments described herein.

The timing diagram illustrated in FIG. 15 illustrates retrograde management in accordance with embodiments described herein. The atrial pace 1510 of the first cardiac cycle is noncaptured. The ventricular pace 1520 of the first cardiac cycle causes retrograde conduction to the atrium. An atrial depolarization 1540 produced by the retrograde conduction causes the atrial tissue to become refractory during a tissue refractory period 1550. The atrial depolarization 1540 does not initiate a new pacing cycle because the atrial depolarization occurs during PVARP 1520. The CRM system senses the atrial depolarization 1540 that occurs during the PVARP 1520. The next scheduled atrial pace 1511 for the cycle following the retrograde conduction is delayed until after the tissue refractory period 1550 ends. Typically the period 1550 of tissue refractoriness lasts less than 300 ms after the depolarization 1540 is sensed, for example. Therefore, the next scheduled atrial pace 1511 in this example is delayed until about 300 ms following the atrial depolarization 1540.

The delayed pace 1511 is correctly classified as a captured pace. The third cardiac cycle includes an atrial pace 1512 and a ventricular pace 1532 that are delivered at the scheduled time.

FIGS. 14 and 15 above illustrate retrograde conduction when the retrograde atrial depolarization occurs during PVARP. In this scenario, the retrograde atrial depolarization does not initiate a new pacing cycle. Retrograde conduction producing atrial depolarizations that occur after PVARP has expired may result in PMT. PMT caused by retrograde conduction is illustrated in the timing diagram of FIG. 16. The first cardiac cycle includes a noncaptured atrial pace 1610 and a captured ventricular pace 1630. PVARP 1620 is timed following the ventricular pace 1630, 1631 for each cycle. The noncaptured atrial pace 1610 in the first cycle allows the depolarization initiated by the captured ventricular pace 1630 of the first cycle to conduct retrogradely to the atrium. An atrial depolarization caused by the retrograde conduction causes a nonrefractory atrial sense. Because the atrial sense 1641 occurs after expiration of PVARP 1620 (i.e., is a nonrefractory sense), the CRM system initiates a pacing cycle in the second cardiac cycle which is abnormally fast. The pattern of fast ventricular paces and retrograde atrial depolarizations that occur after PVARP continues in the third and fourth cycles. The pacing cycles of FIG. 16 illustrate PMT.

Figure 17:
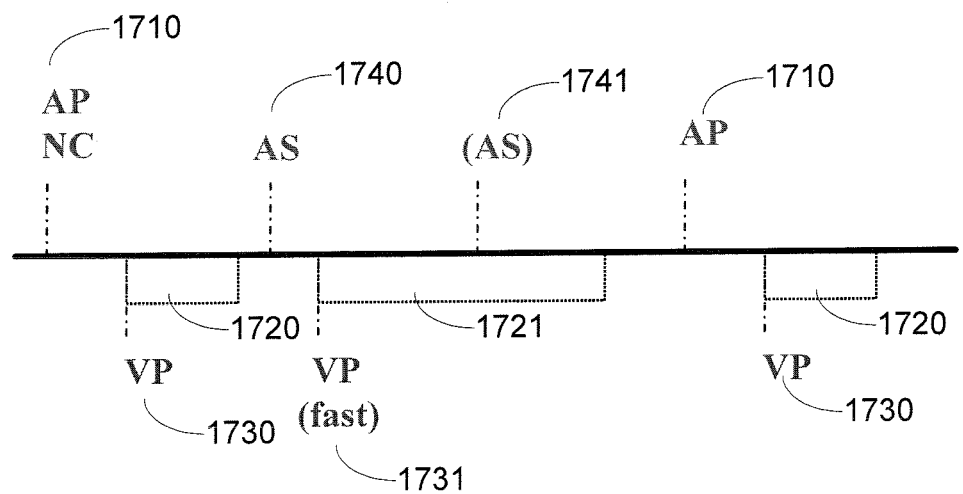
FIG. 17 is a timing diagram illustrating PMT management in accordance with embodiments described herein.

The timing diagram illustrated in FIG. 17 illustrates PMT management in accordance with embodiments described herein. The first pacing cycle includes a noncaptured atrial pace 1710 and a captured ventricular pace 1730. The noncaptured atrial pace 1710 allows the depolarization caused by the ventricular pace to be retrogradely conducted to the atrium. The retrograde conduction occurs after PVARP for the cycle has expired. The nonrefractory atrial sense 1740 caused by the retrograde conduction is used by the CRM system to initiate a pacing cycle. The next ventricular pace 1731 is fast.

The CRM system initiates PMT management following the noncaptured atrial pace 1710 in the first cycle and the nonrefractory atrial sense 1740 initiating the second cycle.

The PVARP 1721 for the pacing cycle following the noncaptured pace 1710, which is the second cycle illustrated in FIG. 17, is extended to break the PMT pattern. The next atrial sense 1741 occurs in the extended PVARP 1721 and does not initiate a pacing cycle. The third cardiac cycle illustrated in FIG. 17 is a normal cycle.

Figure 18:
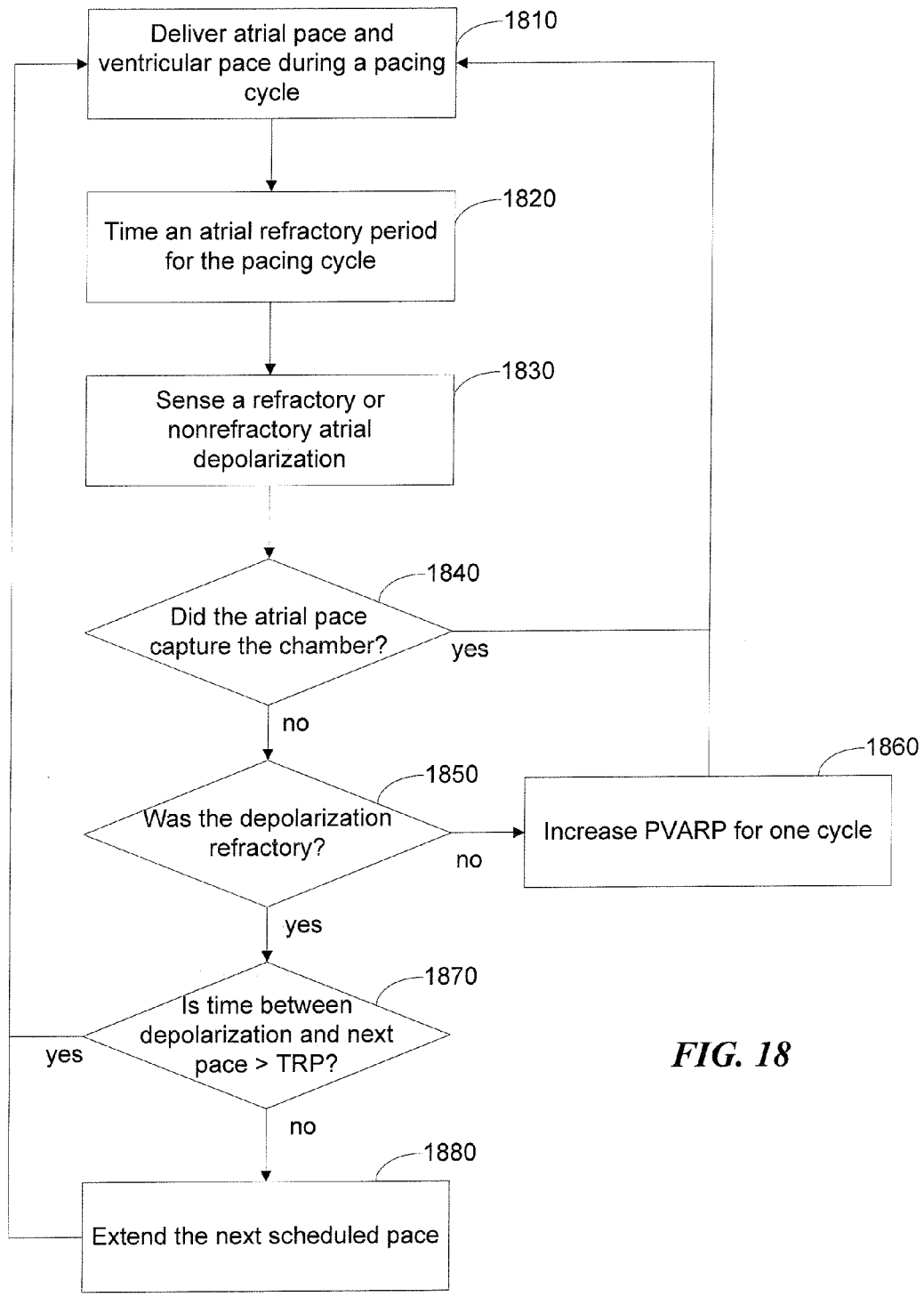
FIG. 18 is a flowchart illustrating retrograde management and PMT management in accordance with embodiments described herein.

The flowchart of FIG. 18 illustrates retrograde conduction management and PMT management in accordance with embodiments described herein. An atrial pace and a ventricular pace are delivered 1810 during a pacing cycle. An atrial refractory period is timed 1820 for the pacing cycle. A refractory or nonrefractory atrial depolarization is sensed 1830. If the atrial pace did not capture 1840 the atrium and the atrial depolarization was sensed 1850 after expiration of the refractory period, then PVARP is increased 1860 for one cardiac cycle. For example, the PVARP may be extended to about 500 ms. Extending the PVARP to 500 ms for one cardiac cycle breaks the PMT.

If the atrial pace did not capture 1840 the atrium and the atrial depolarization was sensed 1850 during the refractory period, the system checks to determine 1870 if the time between the atrial depolarization and the next scheduled atrial pace is greater than the tissue refractory period (TRP). If not, the time for the next scheduled pace is extended 1880 to avoid retrograde conduction in subsequent cardiac cycles. For example, the time for the next pace may be extended so that there is about 300 ms between the refractory atrial sense and the next pace.

It is understood that the components and functionality depicted in the figures and described herein can be implemented in hardware, software, or a combination of hardware and software. It is further understood that the components and functionality depicted as separate or discrete blocks/elements in the figures in general can be implemented in combination with other components and functionality, and that the depiction of such components and functionality in individual or integral form is for purposes of clarity of explanation, and not of limitation.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A cardiac device, comprising:
pacing circuitry for delivering pacing pulses to a cardiac chamber;
sensing circuitry configured to detect cardiac events;
a controller operatively coupled to the pacing circuitry and the sensing circuitry;
the controller configured to control the pacing circuitry to deliver pacing pulses to the cardiac chamber at a first rate prior to initiating a capture threshold test (CTT), and to determine from the detected cardiac events a number of intrinsic and/or fusion beats and count the number of intrinsic and/or fusion beats over a plurality of cardiac cycles;
the controller further configured to set a capture threshold test (CTT) pacing rate for the capture threshold test (CTT), wherein the capture threshold test (CTT) pacing rate is set higher than the first rate if the number of counted intrinsic and/or fusion beats reached a predetermined threshold, while limiting the capture threshold test (CTT) pacing rate from going beyond a predetermined maximum pacing rate; and
after setting the capture threshold test (CTT) pacing rate, the controller configured to initiate the capture threshold test (CTT) at the capture threshold test (CTT) pacing rate by delivering pacing pulses to the cardiac chamber using the pacing circuitry.

2. The cardiac device of claim 1, wherein the plurality of cardiac cycles are a predetermined number of cardiac cycles.

3. The cardiac device of claim 1, wherein the plurality of cardiac cycles are a plurality of consecutive cardiac cycles.

4. The cardiac device of claim 1, wherein the number of counted intrinsic and/or fusion beats corresponds to the number of intrinsic and/or fusion beats that occur in consecutive cardiac cycles.

5. The cardiac device of claim 1, wherein the controller is configured to maintain a previous pacing rate as the capture threshold test (CTT) pacing rate if the number of counted intrinsic and/or fusion beats does not reach the predetermined threshold.

6. The cardiac device of claim 1, wherein the cardiac capture threshold test (CTT) comprises delivering a sequence of pacing pulses at differing energy levels until a predetermined number of noncapture responses are detected.

7. A cardiac device, comprising:
pacing circuitry for delivering pacing pulses to a heart chamber;
sensing circuitry configured to detect cardiac signals that include indications of cardiac events during a plurality of cardiac cycles; and
a controller coupled to the pacing circuitry and the sensing circuitry, the controller configured to count a number of intrinsic beats in the cardiac events prior to initiating a capture threshold test (CTT), the controller further configured to set a capture threshold test (CTT) pacing rate for the capture threshold test (CTT), wherein the capture threshold test (CTT) pacing rate is set at a first pacing rate if the number of intrinsic beats in the cardiac events does not go beyond a predetermined threshold, and the capture threshold test (CTT) pacing rate is set higher at a second pacing rate if the number of intrinsic beats in the cardiac events goes beyond the predetermined threshold; and
after setting the capture threshold test (CTT) pacing rate, the controller is configured to initiate the capture threshold test (CTT) at the capture threshold test (CTT) pacing rate by delivering pacing pulses to the heart chamber using the pacing circuitry.

8. The cardiac device of claim 7, wherein the controller limits the capture threshold test (CTT) pacing rate from going beyond a predetermined maximum pacing rate.

9. The cardiac device of claim 7, wherein prior to initiating a capture threshold test (CTT), the controller is configured to repeatedly count the number of intrinsic beats in the cardiac events, and set the capture threshold test (CTT) pacing rate to higher pacing rate if the number of intrinsic beats in the cardiac events goes beyond the predetermined threshold until the number of intrinsic beats in the cardiac events does not go beyond the predetermined threshold or until a predetermined maximum pacing rate is reached.

10. The cardiac device of claim 9, wherein after the number of intrinsic beats in the cardiac events does not go beyond the predetermined threshold, the controller is configured to initiate the capture threshold test (CTT) at the capture threshold test (CTT) pacing rate.

11. The cardiac device of claim 7, wherein the cardiac capture threshold test (CTT) comprises delivering a sequence of pacing pulses at differing energy levels until a predetermined number of noncapture responses are detected.

* * * * *